(12) United States Patent
Podust et al.

(10) Patent No.: US 7,510,842 B2
(45) Date of Patent: Mar. 31, 2009

(54) BIOMARKER FOR OVARIAN AND ENDOMETRIAL CANCER: HEPCIDIN

(75) Inventors: Valdimir Podust, Fremont, CA (US); Zhen Zhang, Dayton, MD (US); Eric T. Fung, Los Altos, CA (US); Robert Bast, Houston, TX (US); Daniel W. Chan, Clarksville, MD (US); Jin Song, Baltimore, MD (US)

(73) Assignees: Vermilllion, Inc., Fremont, CA (US); The John Hopkins University, Baltimore, MD (US); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 11/373,833

(22) Filed: Mar. 10, 2006

(65) Prior Publication Data

US 2007/0054329 A1    Mar. 8, 2007

Related U.S. Application Data

(60) Provisional application No. 60/662,090, filed on Mar. 11, 2005.

(51) Int. Cl.
 *G01N 33/53* (2006.01)
(52) U.S. Cl. ........................ 435/7.1; 435/7.23
(58) Field of Classification Search ........................ None
 See application file for complete search history.

(56) References Cited

FOREIGN PATENT DOCUMENTS

WO    WO-2004/012588    2/2004

OTHER PUBLICATIONS

Kemna et al, Clin Chem, 2007, 53:620-628.*
Brugnara, Clin Chem 2003, 49:1573-1578.*
Weinstein et al, Blood, 2002, 100:3776-3781.*
Vita et al, J Inerferon Cytokine Res, 2001, 21:45-52.*
Andrews, J Cline Inves, 2004, 113:1251-1253.
Tempfer et al., Gynecol Oncol, 1997, 66:27-30.
Sarjadi et al., Gynecol Oncol 1980, 10:113-124.

* cited by examiner

*Primary Examiner*—Misook Yu
*Assistant Examiner*—Mark Halvorson
(74) *Attorney, Agent, or Firm*—Edwards Angell Palmer & Dodge LLP; Peter F. Corless; Jonathan M. Sparks

(57) ABSTRACT

The present invention provides protein-based biomarkers and biomarker combinations that are useful in qualifying ovarian cancer status as well as endometrical cancer status in a patient. In particular, it has been found that hepcidin is a biomarker for both ovarian cancer and endometrial cancer and that a panel of biomarkers, including hepcidin, transthyretin and optionally other markers are useful to classify a subject sample as ovarian cancer or non-ovarian cancer. The biomarkers can be detected by SELDI mass spectrometry.

14 Claims, 17 Drawing Sheets

Ovarian ca vs. HC

|  | pI/Mw(M+H) |
|---|---|
| SWMPMFQRRRRRDTHFPICIFCC GCCHRSKCGM CCKT | 9.37 / 4487.44 |
| WMPMFQRRRRRDTHFPICIFCC GCCHRSKCGM CCKT | 9.37 / 4400.37 |
| MPMFQRRRRRDTHFPICIFCC GCCHRSKCGM CCKT | 9.37 / 4214.15 |
| PMFQRRRRRDTHFPICIFCC GCCHRSKCGM CCKT | 9.39 / 4082.96 |
| MFQRRRRRDTHFPICIFCC GCCHRSKCGM CCKT | 9.37 / 3985.84 |
| FQRRRRRDTHFPICIFCC GCCHRSKCGM CCKT | 9.37 / 3854.65 |
| QRRRRRDTHFPICIFCC GCCHRSKCGM CCKT | 9.37 / 3707.47 |
| RRRRRDTHFPICIFCC GCCHRSKCGM CCKT | 9.37 / 3579.34 |
| RRRRDTHFPICIFCC GCCHRSKCGM CCKT | 9.17 / 3423.16 |
| RRRDTHFPICIFCC GCCHRSKCGM CCKT | 8.97 / 3266.97 (4-s-s, oxid. of Met. 3275 Da) |
| RRDTHFPICIFCC GCCHRSKCGM CCKT | 8.76 / 3110.78 |
| RDTHFPICIFCC GCCHRSKCGM CCKT | 8.53 / 2954.59 |
| DTHFPICIFCC GCCHRSKCGM CCKT | 8.22 / 2798.41 (Hepcidin 25) |
| THFPICIFCC GCCHRSKCGM CCKT | 8.51 / 2682.32 (Hepcidin 24) |
| HFPICIFCC GCCHRSKCGM CCKT | 8.53 / 2581.21 |
| FPICIFCC GCCHRSKCGM CCKT | 8.53 / 2444.07 (Hepcindin-22) |
| PICIFCC GCCHRSKCGM CCKT | 8.60 / 2296.89 |
| ICIFCC GCCHRSKCGM CCKT | 8.53 / 2199.78 (Hepcidin-20) |
| CIFCC GCCHRSKCGM CCKT | 8.53 / 2086.62 |
| CIFCC GCCHRSKCGM CCK | 8.53 / 1985.51 |
| CIFCC GCCHRSKCGM CC | 8.22 / 1857.34 |

Fig. 2

SELDI Spectrum of serum sample after immunoprecipitation/pull-down using Ab against ITIH4 fragment (m/z 3272) peaks in rectangle labels are known fragment of ITIH4. The discovered four hepcidin variants are in this spectrum at approximate m/z locations 2191, 2436, 2673, and 2788 (indicated by the red arrows).

ROC curve analysis showing the discriminatory power of one of the hepcidin peaks for the two independent validation sets. The AUCs are 0.756 and 0.772, both greater than 0.5 with p-value<0.0001.

Scatterplot of the five groups of samples in two of the four peaks representing hepcidin variants.

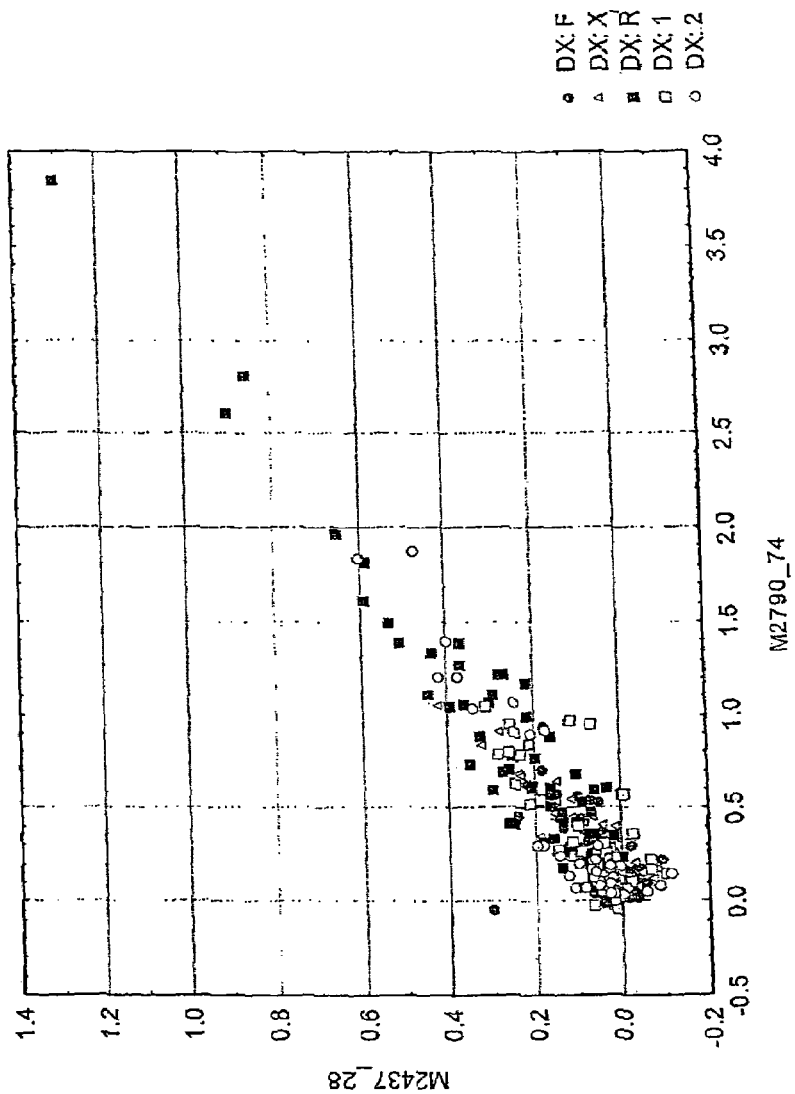

Fig. 7

Scatterplot of five groups of patients from an independent validation set using two of the hepcidin peaks. It shows that these peaks are lower in patients free of cancer and patients after treatment and are higher in patients with ovarian cancer pretreatment and those with recurrent ovarian cancer. The hepcidin level seems to reflect the tumor load.

F: Free of Ca, X: mismatched, R: recurrent, 1: pre-Treatment, 2: after Treatment.

Scatterplot of five groups of patients from a second independent validation set using two of the hepcidin peaks. It shows that these peaks are lower in healthy controls and patients with benign diseases, and are higher in patients with ovarian cancer H: Healthy, B: Benign, C: Cancer.

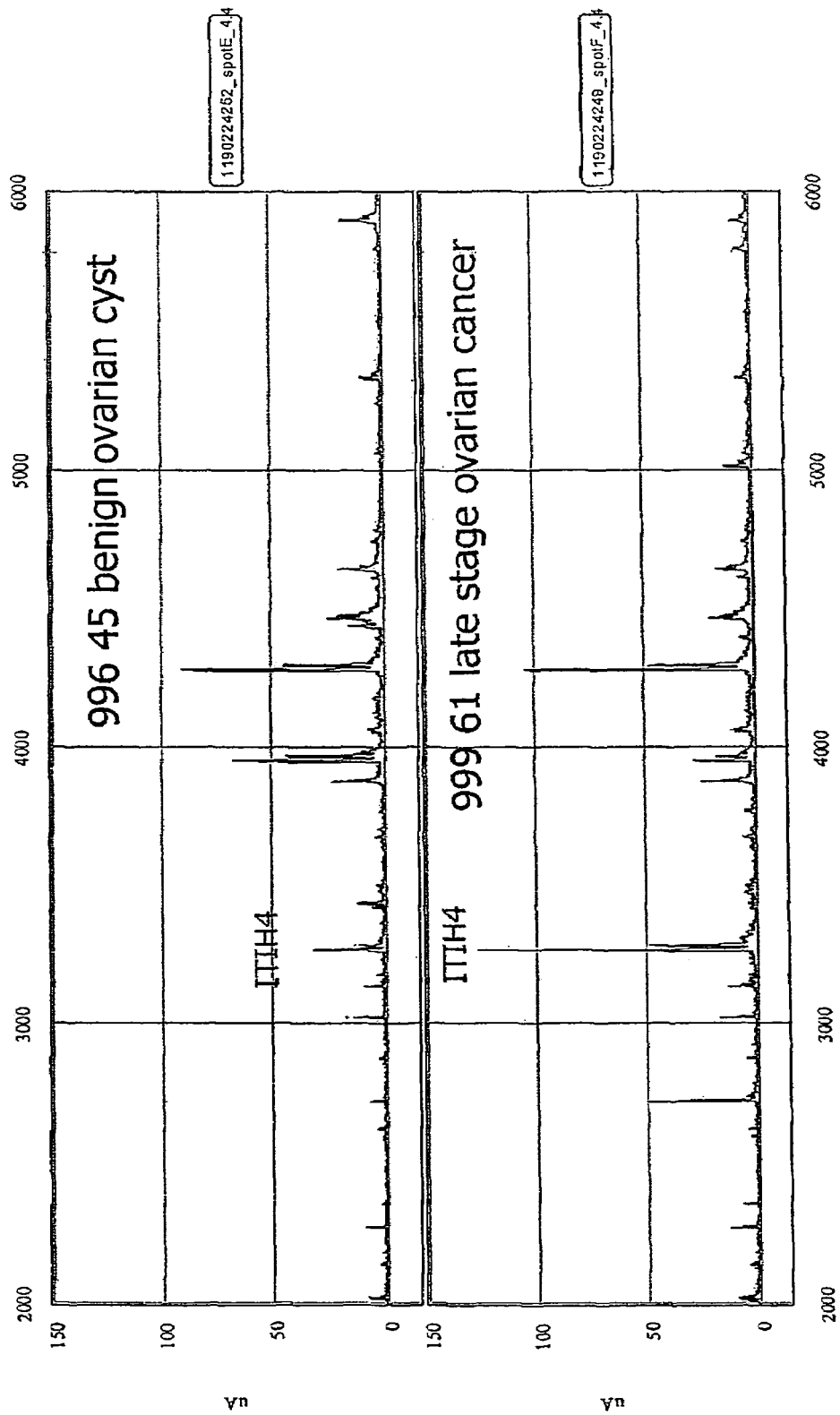

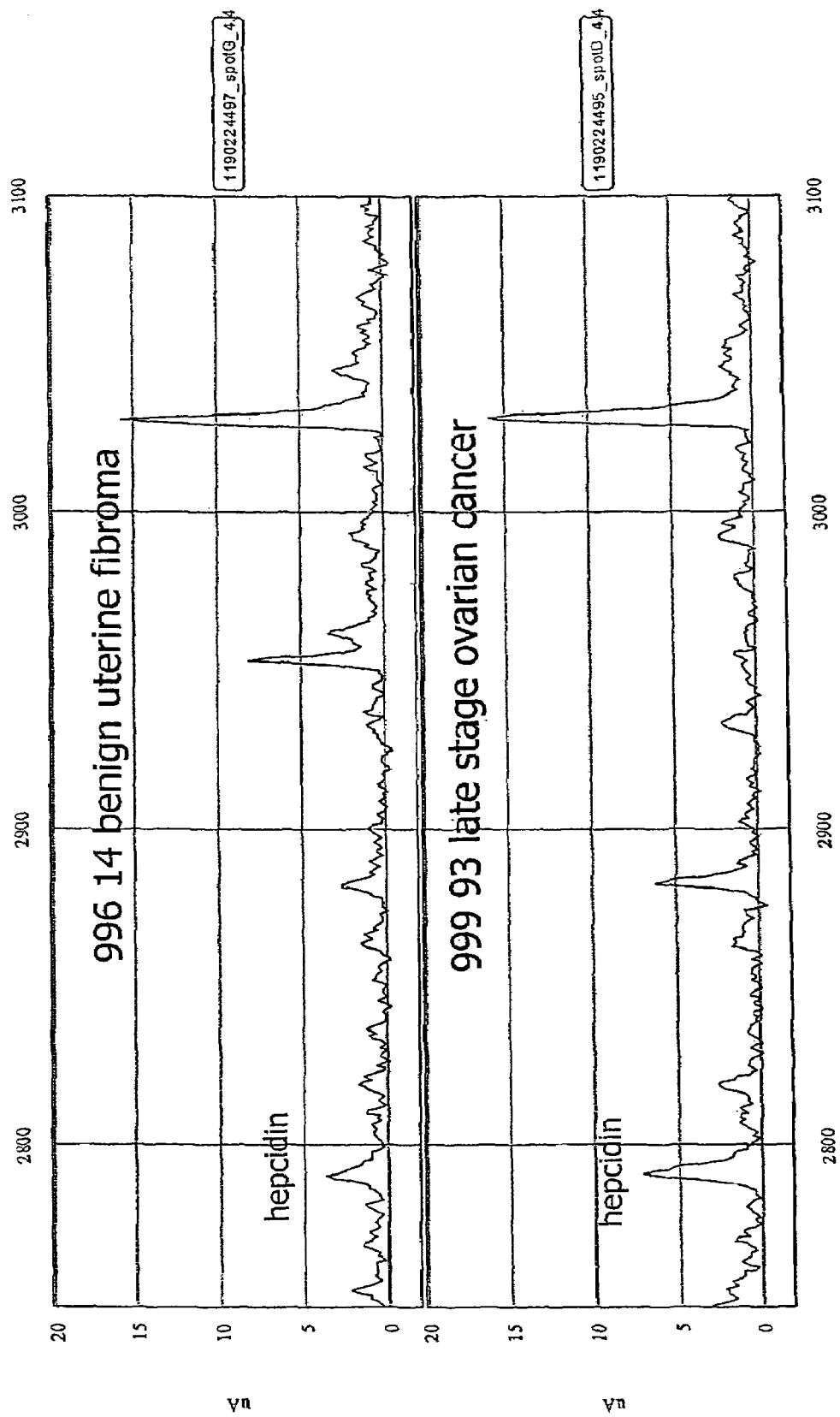

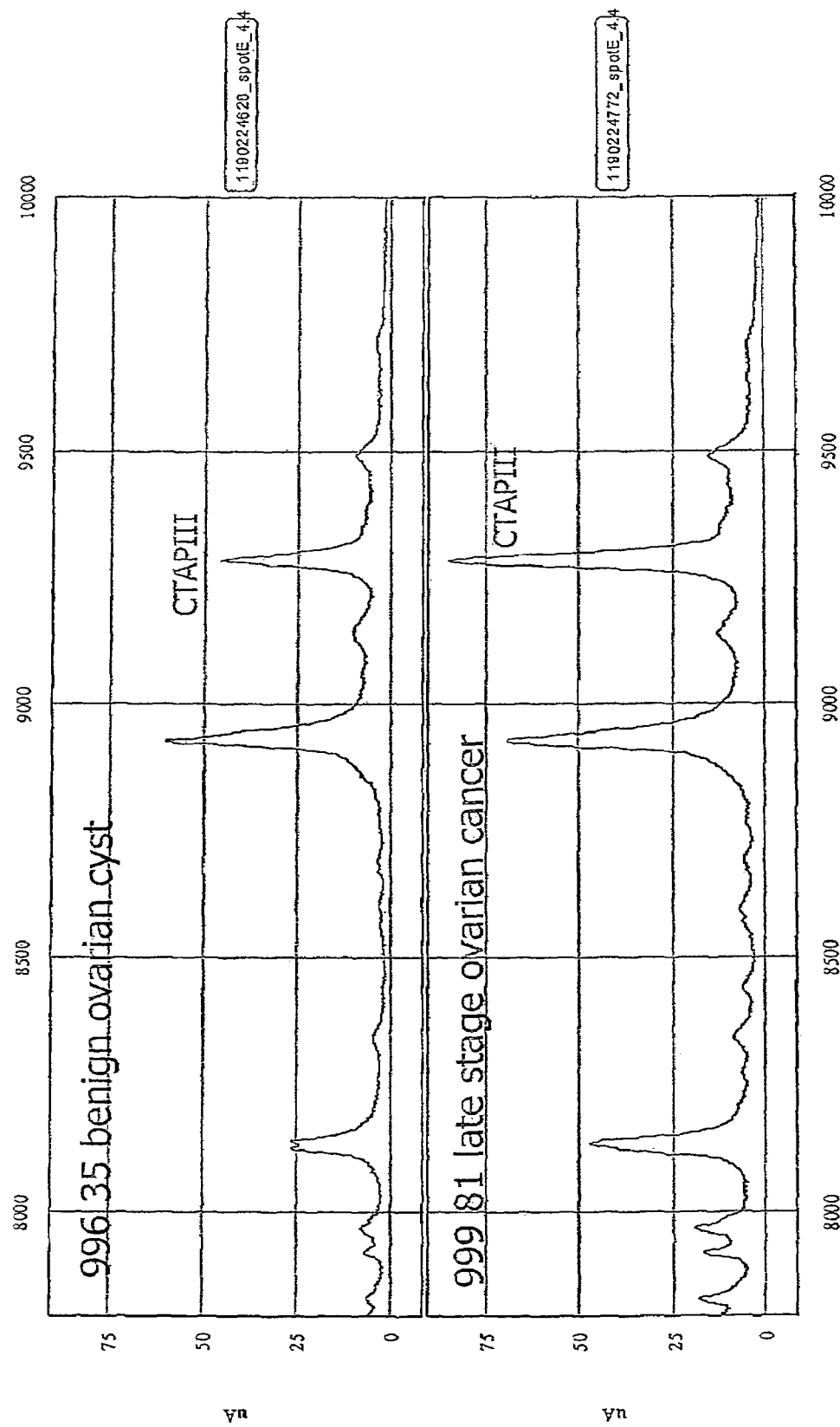

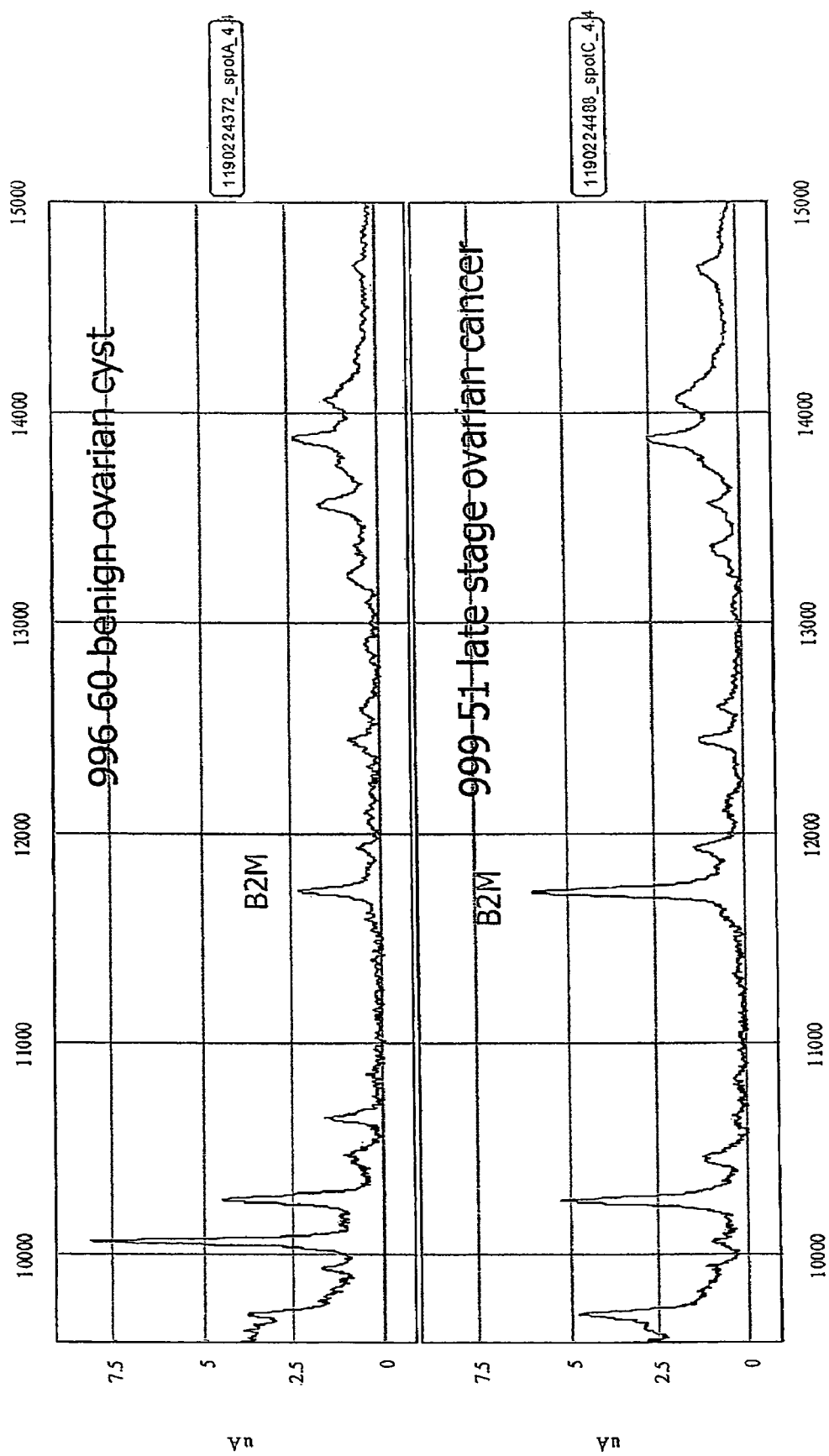

Transthyretin on Q10

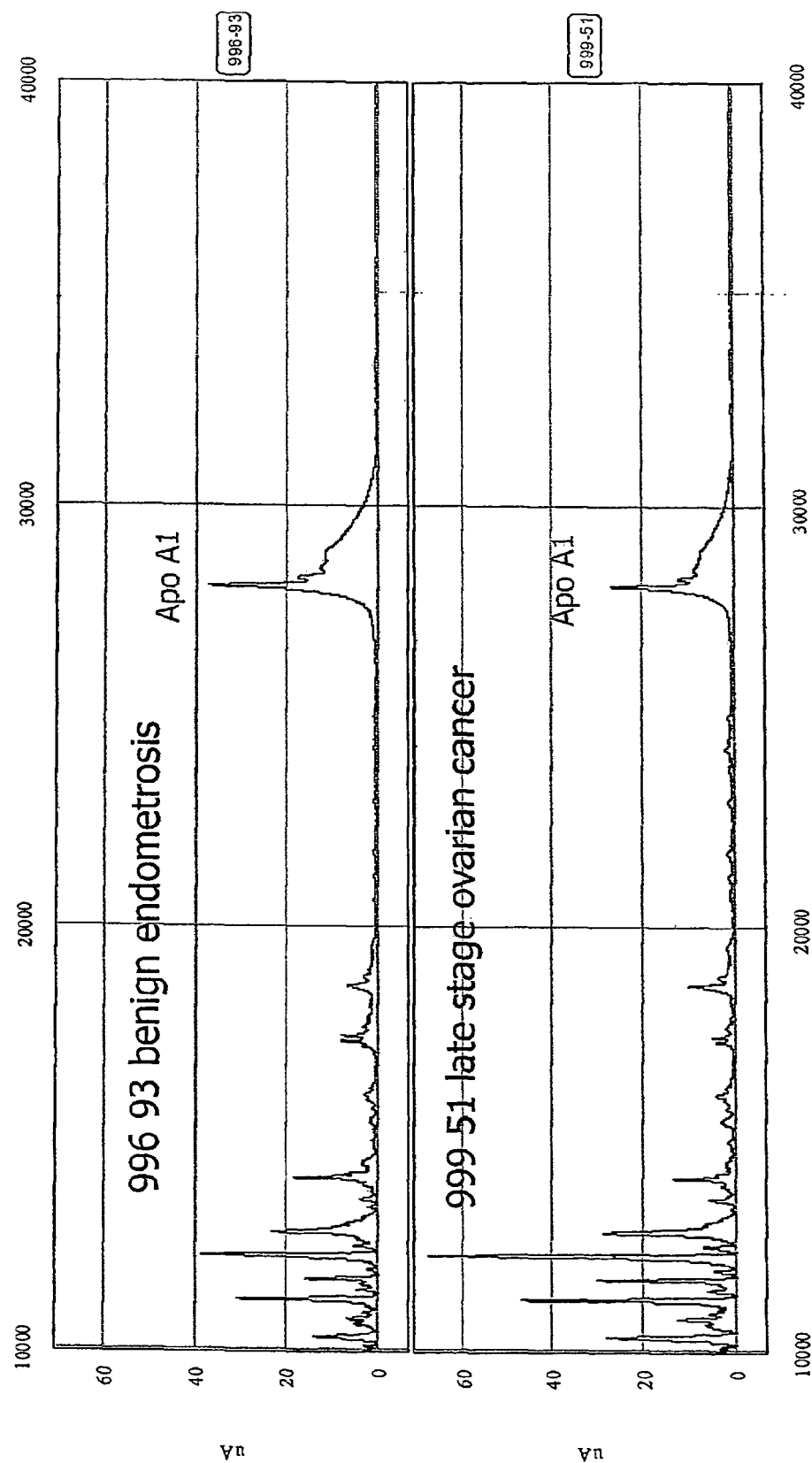

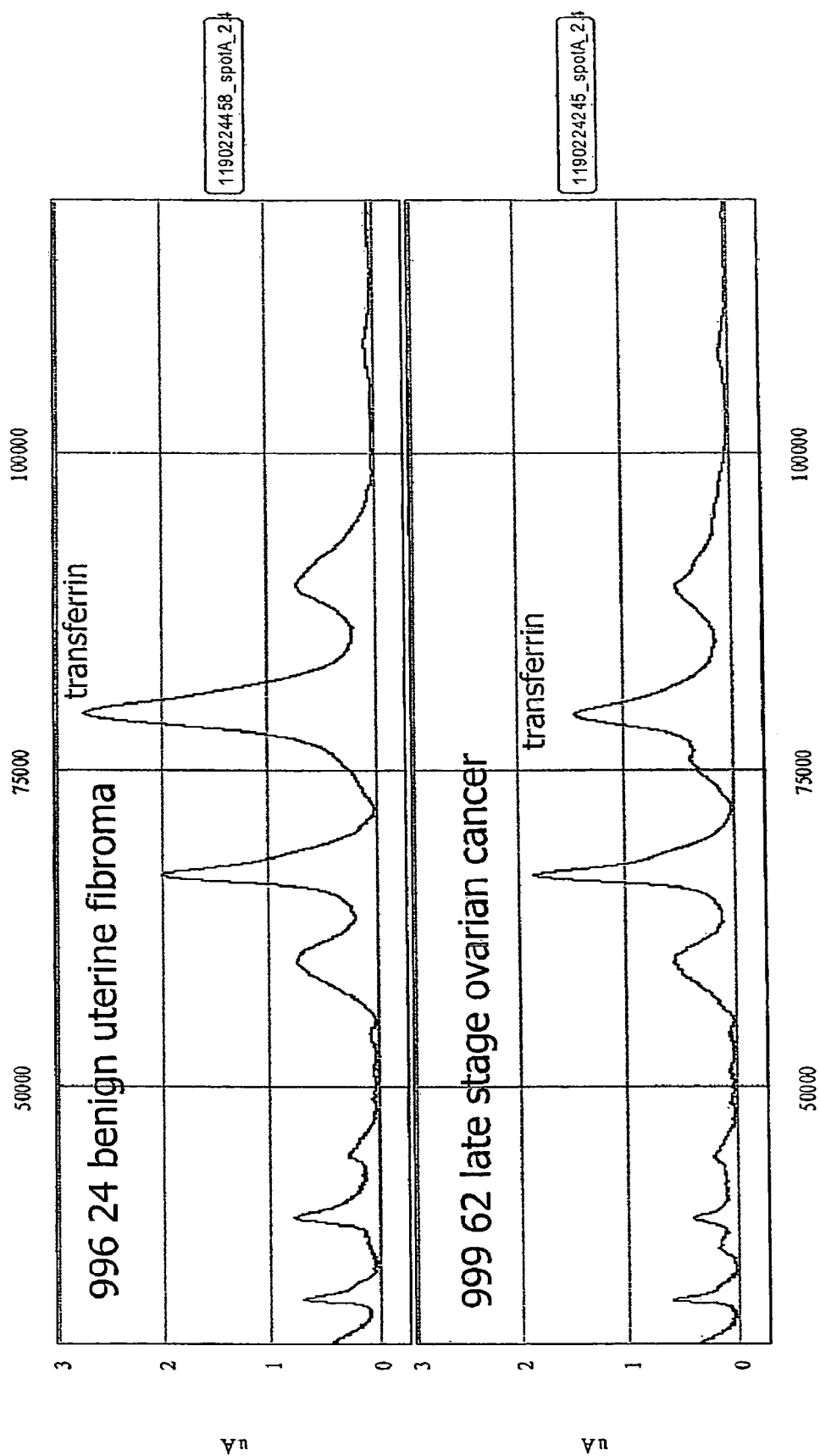
Fig. 9G: Transferrin on IMAC50

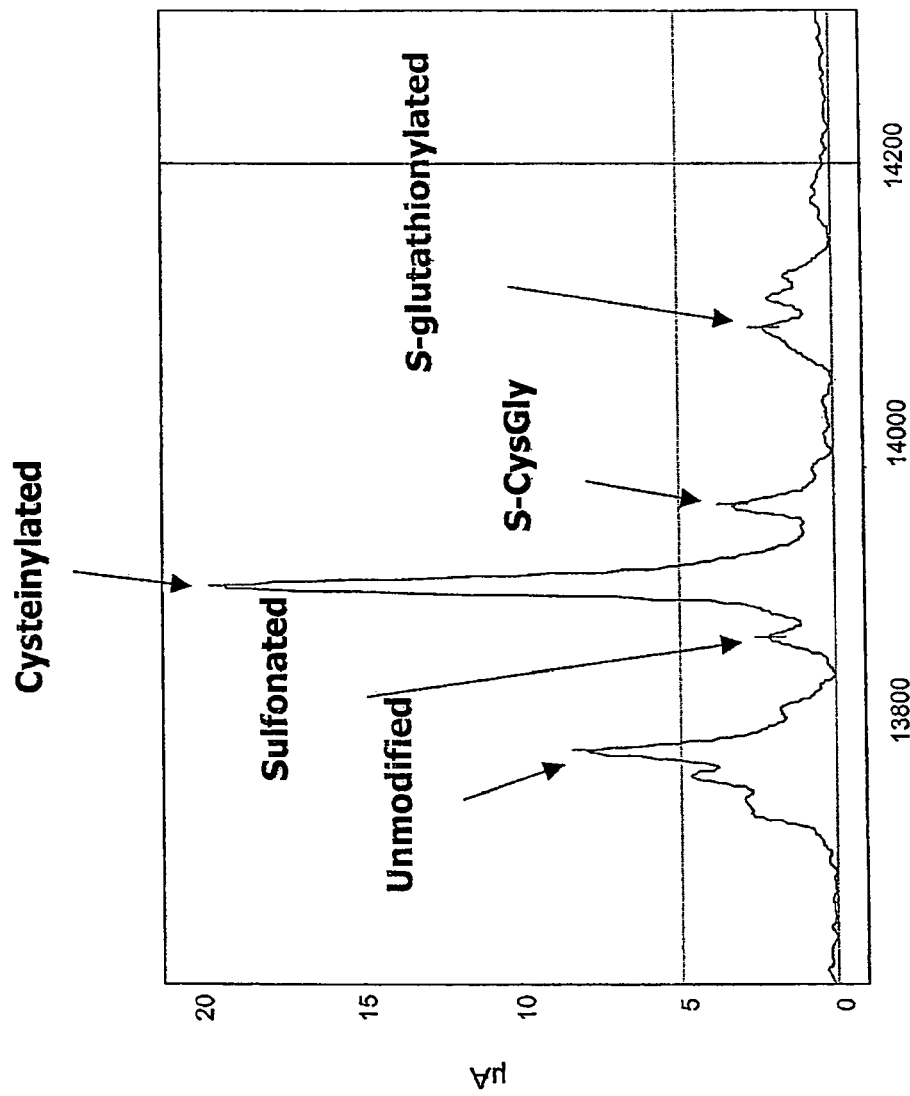
FIG: 10: Transthyretin peaks on Q10 array

US 7,510,842 B2

BIOMARKER FOR OVARIAN AND ENDOMETRIAL CANCER: HEPCIDIN

The present application claims the benefit of U.S. provisional application No. 60/662,090 filed Mar. 11, 2005, which is incorporated herein by reference in its entirety.

FIELD OF THE INVENTION

The invention relates generally to clinical diagnostics.

BACKGROUND OF THE INVENTION

Ovarian cancer is among the most lethal gynecologic malignancies in developed countries. Annually in the United States alone, approximately 23,000 women are diagnosed with the disease and almost 14,000 women die from it. (Jamal, A., et al., CA Cancer J. Clin, 2002; 52:23-47). Despite progress in cancer therapy, ovarian cancer mortality has remained virtually unchanged over the past two decades. (Id.) Given the steep survival gradient relative to the stage at which the disease is diagnosed, early detection remains the most important factor in improving long-term survival of ovarian cancer patients.

The poor prognosis of ovarian cancer diagnosed at late stages, the cost and risk associated with confirmatory diagnostic procedures, and its relatively low prevalence in the general population together pose extremely stringent requirements on the sensitivity and specificity of a test for it to be used for screening for ovarian cancer in the general population.

The identification of tumor markers suitable for the early detection and diagnosis of cancer holds great promise to improve the clinical outcome of patients. It is especially important for patients presenting with vague or no symptoms or with tumors that are relatively inaccessible to physical examination. Despite considerable effort directed at early detection, no cost effective screening tests have been developed (Paley P J., Curr Opin Oncol, 2001; 13(5):399-402) and women generally present with disseminated disease at diagnosis. (Ozols R F, et al., Epithelial ovarian cancer. In: Hoskins W J, Perez C A, Young R C, editors. Principles and Practice of Gynecologic Oncology. 3rd ed. Philadelphia: Lippincott, Williams and Wilkins; 2000. p. 981-1057).

The best-characterized tumor marker, CA125, is negative in approximately 30-40% of stage I ovarian carcinomas and its levels are elevated in a variety of benign diseases. (Meyer T, et al., Br J Cancer, 2000;82(9):1535-8; Buamah P., *J Surg Oncol*, 2000;75(4):264-5; Tuxen M K, et al., *Cancer Treat Rev*, 1995;21(3):215-45). Its use as a population-based screening tool for early detection and diagnosis of ovarian cancer is hindered by its low sensitivity and specificity. (MacDonald N D, et al., *Eur J Obstet Gynecol Reprod Biol*, 1999; 82(2):155-7; Jacobs I, et al., *Hum Reprod*, 1989;4(1):1-12; Shih I-M, et al., Tumor markers in ovarian cancer. In: Diamandis E P, Fritsche, H., Lilja, H., Chan, D. W., and Schwartz, M., editor. Tumor markers physiology, pathobiology, technology and clinical applications. Philadelphia: AACC). Although pelvic, and more recently, vaginal sonography has been used to screen high-risk patients, neither technique has sufficient sensitivity and specificity to be applied to the general population. (MacDonald N D, et al., supra). Recent efforts in using CA125 in combination with additional tumor markers (Woolas R P X F, et al., *J Natl Cancer Inst*, 1993;85 (21):1748-51; Woolas R P, et al., *Gynecol Oncol*, 1995;59(1): 111-6; Zhang Z, et al., *Gynecol Oncol*, 1999;73(1):56-61; Zhang Z, et al., Use of Multiple Markers to Detect Stage I Epithelial Ovarian Cancers: Neural Network Analysis Improves Performance. American Society of Clinical Oncology 2001; Annual Meeting, Abstract) in a longitudinal risk of cancer model (Skates S J, et al., *Cancer*, 1995;76(10 Suppl): 2004-10), and in tandem with ultrasound as a second line test (Jacobs I D A, et al., *Br Med J*, 1993;306(6884):1030-34; Menon U TA, et al., *British Journal of Obstetrics and Gynecology*, 2000;107(2):165-69) have shown promising results in improving overall test specificity, which is critical for a disease such as ovarian cancer that has a relatively low prevalence. See also Menon et al. J. Clin. Oncology (2005) 23(31): 7919-26.

Due to the dismal prognosis of late stage ovarian cancer, it is the general consensus that a physician will accept a test with a minimal positive predictive value of 10%. (Bast, R. C., et al., Cancer Treatment and Research, 2002; 107:61-97). Extending this to the general population, a general screening test would require a sensitivity greater than 70% and a specificity of 99.6%. Currently, none of the existing serologic markers, such as CA125, CA72-4, or M-CSF, individually delivers such a performance. (Bast, R. C., et al., Int J Biol Markers, 1998; 13:179-87).

Thus, there is a critical need for new serological markers that individually or in combination with other markers or diagnostic modalities deliver the required sensitivity and specificity for early detection of ovarian cancer. (Bast R C, et al., Early detection of ovarian cancer: promise and reality. Ovarian Cancer: ISIS Medical Media Ltd., Oxford, UK).

Given the low incidence of ovarian cancer, a screening test intended for the asymptomatic woman with adequate positive predictive remains elusive. It has been demonstrated, however, that even in the absence of a general screening test, one factor that does improve long-term survival of patients with ovarian cancer is appropriate triage to the specialist gynecologic oncologist (Craig, C C et al, Effect of surgeon specialty on processes of care and outcomes for ovarian cancer patients, J Natl Canc Inst, 2006:98, 172-80). This is particularly true of women who present to their physician with symptoms suggestive of a pelvic mass.

Thus, it is desirable to have a reliable and accurate method of determining the ovarian cancer status in patients, the results of which can then be used to manage subject treatment.

SUMMARY OF THE INVENTION

It has been found that hepcidin is a biomarker for ovarian cancer (invasive epithelial cancer). It has further been found that hepcidin is a biomarker that is differentially present in subjects having endometrial cancer. More particularly, it has been found that the hepcidin level in a biological sample is increased in ovarian cancer versus non-ovarian cancer and in endometrial cancer versus non-endometrial cancer. Put another way, elevated hepcidin levels are correlated with ovarian cancer and with endometrial cancer.

In certain embodiments, the disease statuses to be distinguished are: ovarian cancer versus benign ovarian disease; ovarian cancer versus benign gynecologic disease; ovarian cancer versus a gynecological condition selected from endometriosis, uterine fibroma, breast cancer and cervical cancer; ovarian versus other malignancy (e.g., breast cancer or colon cancer); stage I ovarian cancer versus non-ovarian cancer; and recurrence of ovarian cancer versus non-ovarian cancer. Based on the status determined, further procedures may be indicated, including additional diagnostic tests or therapeutic procedures or regimens.

It has further been found that when hepcidin level is used in combination with the level of other biomarkers, the predictive power of the diagnostic test is improved. More specifically, increased levels of hepcidin and decreased levels transthyretin are correlated with ovarian cancer. Increased levels of hepcidin and decreased levels of transthyretin, together with levels of one or more of Apo A1 (decreased level), transferrin (decreased level), CTAP-III (elevated level) and an internal fragment of ITIH4 (elevated level) also are correlated with ovarian cancer. These biomarkers can be further combined with β-2 microglobulin (elevated level), CA125 (elevated level) and/or other known ovarian cancer biomarkers in the diagnostic test.

In one aspect, the present invention provides methods for qualifying ovarian cancer status in a subject comprising measuring one or more biomarkers in a biological sample from the subject, wherein at least one biomarker is hepcidin, and correlating the measurement or measurements with an ovarian cancer status selected from ovarian cancer and non-ovarian cancer. In one embodiment of such methods, a plurality of biomarkers in the biological sample are measured, wherein the measured biomarkers further comprise transthyretin in addition to hepcidin. In another embodiments of such methods, a plurality of biomarkers in the biological sample are measured, wherein the measured biomarkers further comprise in addition to hepicidin at least one biomarker selected from the group consisting of: Apo A1, transferrin, CTAP-III and ITIH4 fragment. In a further aspect of such methods, a plurality of biomarkers in the biological sample are measured, wherein the measured biomarkers further comprise in addition to hepcidin at least two biomarkers selected from the group consisting of Apo A1, transferrin, CTAP-III and ITIH4 fragment. In a yet further aspect of such methods, a plurality of biomarkers in the biological sample are measured, wherein the measured biomarkers further comprise in addition to hepcidin at least three biomarkers selected from the group consisting of Apo A1, transferrin, CTAP-III and ITIH4 fragment. In a still further aspect, a plurality of biomarkers are measured, and the measured biomarkers comprise β-2 microglobulin.

In one embodiment, hepcidin may be hepcidin-25, transthyretin may be cysteinylated transthyretin, and/or ITIH4 fragment may be ITIH4 fragment 1.

In another embodiment, one or more biomarkers are measured by mass spectrometry. The mass spectrometry suitably may be SELDI-MS. In a further aspect, one or more biomarkers are measured by immunoassay.

A variety of biological samples may be employed in methods of the invention, including e.g. where the biological sample comprises blood or a blood derivative, or where the biological sample comprises ovarian cyst fluid, ascites, or urine.

In one embodiment of methods of the invention, wherein non-ovarian cancer is benign ovarian disease. In another embodiment, non-ovarian cancer is a gynecological condition such as benign ovarian cyst, endometriosis, uterine fibroma, breast cancer and cervical cancer. In a further embodiment, the ovarian cancer is stage I or II ovarian cancer. In certain aspects, the subject has been treated for ovarian cancer and the ovarian cancer is recurrence of cancer.

In another aspect, methods are provided for qualifying endometrial cancer status is a subject comprising (a) measuring one or more biomarkers in a biological sample from the subject, wherein at least one biomarker is hepcidin; and (b) correlating the measurement or measurements with endometrial cancer status. In one embodiment, the status is endometrial cancer versus non-cancer.

Methods of the invention may further comprises reporting the status to the subject, recording the status on a tangible medium, and/or managing subject treatment based on the status. One or more biomarker may be after subject management and the measurement correlated with disease progression.

In a preferred aspect, methods are provided for determining the course of ovarian cancer comprising (a) measuring, at a first time, one or more biomarkers in a biological sample from the subject, wherein at least one biomarker is hepcidin; (b) measuring, at a second time, at least one biomarker in a biological sample from the subject; and (c) comparing the first measurement and the second measurement; wherein the comparative measurements determine the course of the ovarian cancer.

In a further preferred aspect, methods are provided that comprise measuring hepcidin and transthyretin in a sample from a subject. In certain embodiments, such methods may further comprise measuring at least one of Apo A1, transferrin, CTAP-III and ITIH4 fragment in the sample.

In another embodiment, the invention provides a kit that comprises (a) a solid support comprising at least one capture reagent attached thereto, wherein the capture reagent binds hepcidin; and (b) instructions for using the solid support to detect hepcidin. The solid support may comprise e.g. a SELDI probe. The kit also may optionally comprise a standard reference of hepcidin.

In a further embodiment, the invention provides a kit that comprises (a) at least one solid support comprising at least one capture reagent attached thereto, wherein the capture reagent binds or reagents bind hepcidin and transthyretin; and (b) instructions for using the solid support or supports to detect hepcidin and transthyretin. The solid support may comprise e.g. a SELDI probe. The kit also may optionally comprise a standard reference of hepcidin and transthyretin.

In a yet further embodiment, the invention provides a kit that comprises (a) at least one solid support comprising at least one capture reagent attached thereto, wherein the capture reagent or reagents bind hepcidin, transthyretin and at least one of Apo A1, transferrin, CTAP-III and ITIH4 fragment; and (b) instructions for using the solid support or supports to detect hepcidin, transthyretin and at least one of Apo A1, transferrin, CTAP-III and ITIH4 fragment. The solid support may comprise e.g. a SELDI probe. The kit also may optionally comprise a standard reference of hepcidin and transthyretin and at least one of Apo A1, transferrin, CTAP-III and ITIH4 fragment.

The invention further includes software products that comprise (a) code that accesses data attributed to a sample, the data comprising measurement of at least one biomarker in the sample, wherein at least one biomarker is hepcidin; and (b) code that executes a classification algorithm that classifies the ovarian cancer status of the sample as a function of the measurement. In one aspect, the at least one biomarker further comprises transthyretin. In another aspect, the at least one biomarker further comprises at least one biomarker selected from Apo A1, transferrin, CTAP-III and ITIH4 fragment. In a yet further aspect, the at least one biomarker further comprises β2-microglobulin.

The invention also provides methods comprising communicating to a subject a diagnosis relating to ovarian cancer status determined from the correlation of at least one biomarker in a sample from the subject, wherein at least one biomarker is hepcidin. In one aspect, the at least one biomarker further comprises transthyretin. The diagnosis may be suitably communicated to the subject e.g. via a computer-generated medium.

The invention further provides methods for identifying a compound that interacts with hepcidin, wherein said method comprises a) contacting hepcidin with a test compound; and b) determining whether the test compound interacts with hepcidin.

Other aspects of the invention are discussed infra.

BRIEF DESCRIPTION OF THE DRAWINGS

FIG 2. shows the sequences of various hepcidin fragments, including the four correlated fragments, hepcidin-25 (SEQ ID NO: 13), hepcidin-24 (SEQ ID NO: 14), hepcidin-22 (SEQ ID NO: 16), and hepcidin-20 (SEQ ID NO: 18). The 21 sequences are numbered SEQ ID NO: 1 through SEQ ID NO: 21 from top to bottom.

FIG. 7 shows a scatterplot of five groups of patients from an independent validation set using two of the hepcidin peaks. It shows that these peaks are lower in patients free of cancer and patients after treatment, and are higher in patients with ovarian cancer pretreatment, as well as in those with recurrent ovarian cancer. The hepcidin level correlates with the tumor load.

FIGS. 9A-9G show SELDI mass spectra displaying various biomarkers mentioned herein. FIG. 9A shows ITIH4 fragment 1 captured on an IMAC-50 biochip charged with copper. FIG. 9B shows hepcidin-25 captured on an IMAC-50 biochip charged with copper. FIG. 9C shows CTAP-III captured on an IMAC-50 biochip charged with copper. FIG. 9D shows β2 microglobulin captured on an IMAC-50 biochip charged with copper. FIG. 9E shows transthyretin captured on a Q-10 biochip. FIG. 9F shows Apo A1 captured on an H50 biochip. FIG. 9G shows transferrin captured on an IMAC-50 biochip charged with copper.

FIG. 10 shows a close-up of a mass spectrum of forms of transthyretin in serum.

DETAILED DESCRIPTION OF THE INVENTION

1. Introduction

Figure 1:
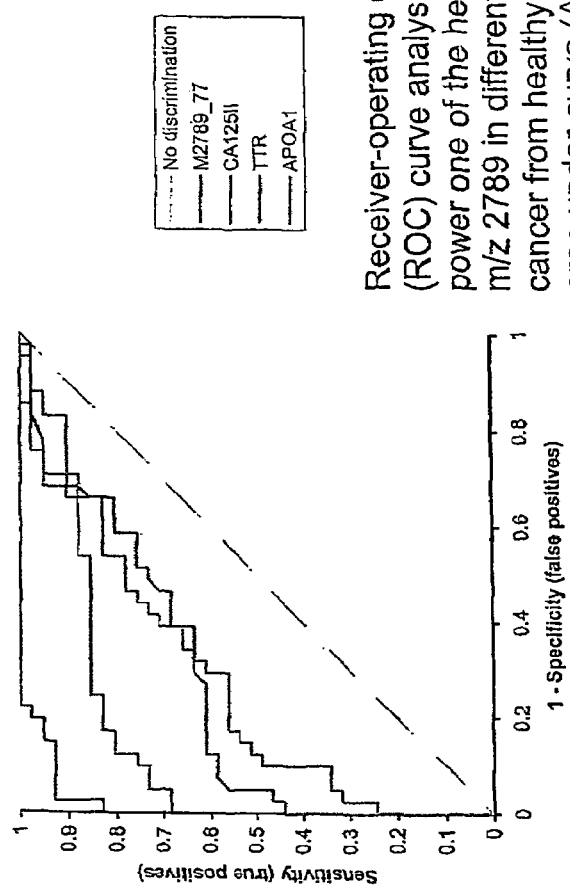
FIG. 1 shows ROC curve analysis showing the power of the hepcidin peak at m/z 2789 has in differentiating ovarian cancer from healthy controls. The AUC is 0.876 and is significantly greater than 0.5 with p-value <0.0001.

A biomarker is an organic biomolecule which is differentially present in a sample taken from a subject of one phenotypic status (e.g., having a disease) as compared with another phenotypic status (e.g., not having the disease). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. As such, they are useful as markers for disease (diagnostics), therapeutic effectiveness of a drug (theranostics) and of drug toxicity.

Biomarkers of this invention were discovered using SELDI. Accordingly, they are characterized, in part, by their mass-to-charge ratio, the shape of the peak in a mass spectrum and their binding characteristics. These characteristics represent inherent characteristics of the biomolecule and not process limitations in the manner in which the biomolecule is discriminated.

Biomarkers of this invention are characterized in part by their mass-to-charge ratio. The mass-to-charge ratio of each biomarker is provided herein. A particular molecular marker designated, for example, as "M2789" has a measured mass-to-charge ratio of 2789 D. The mass-to-charge ratios were determined from mass spectra generated on a Ciphergen Biosystems, Inc. PBS II mass spectrometer or a Ciphergen PCS 4000 mass spectrometer. The PBS II is instrument has a mass accuracy of about +/−0.15 percent. Additionally, the instrument has a mass resolution of about 400 to 1000 m/dm, where m is mass and dm is the mass spectral peak width at 0.5 peak height. The PCS4000 instrument has a mass accuracy of about +/−0.12% raw data with an expected externally calibrated mass accuracy of 0.1% and internally calibrated mass accuracy of 0.01%. Additionally, the instrument has a mass resolution of about 1000 to 2000 m/dm, where m is mass and dm is the mass spectral peak width at 0.5 peak height. The mass-to-charge ratio of the biomarkers was determined using Biomarker Wizard™ software (Ciphergen Biosystems, Inc.). Biomarker Wizard assigns a mass-to-charge ratio to a biomarker by clustering the mass-to-charge ratios of the same peaks from all the spectra analyzed, as determined by the PBSII or PCS4000, taking the maximum and minimum mass-to-charge-ratio in the cluster, and dividing by two. Accordingly, the masses provided reflect these specifications.

Biomarkers of this invention are further characterized by the shape of their spectral peak in time-of-flight mass spectrometry. Mass spectra showing peaks representing the biomarkers are presented in the Figures.

Biomarkers of this invention also are characterized by their binding characteristics to adsorbent surfaces. The binding characteristics of each biomarker also are described herein.

2. Biomarkers for Ovarian Cancer 2.1. Hepcidin

Hepcidin was originally identified as a 25 amino acid peptide (hepcidin-25) in human plasma and urine, exhibiting antimicrobial activity. The full-length hepcidin precursor is an 84 amino acid protein (SwissProt Accession No. P81172) comprising a signal sequence and a pro-region (see Kulaksiz, H. et al. (2004) Gut 53:735-743). The hepcidin biomarkers of the present invention are derived from the C-terminus of the full-length hepcidin protein. Hepcidin is recognized by antibodies available from, e.g., U.S. Biological (catalog H2008-51) (on the world wide web at usbio.net, Swampscott, Mass.). Four different variants of hepcidin useful as biomarkers of this invention are characterized by calculated mass-to-charge ratios of 2789, 2673, 2436, and 2191.

Hepcidin was discovered to be a biomarker for ovarian and endometrial cancer using SELDI technology employing ProteinChip arrays from Ciphergen Biosystems, Inc. (Fremont, Calif.) ("Ciphergen"). More specifically, hepcidin levels can distinguish ovarian cancer from each of non-cancer, cervical cancer and benign ovarian disease. It also can distinguish between endometrial cancer and non-cancer. Urine and serum samples were collected from subjects diagnosed with ovarian cancer, endometrial cancer, cervical cancer and subjects diagnosed as normal or as having benign disease. The samples were applied to SELDI biochips, with or without co-immunoprecipitation with the ITIH4 3272 m/z fragment (see International Publication Number WO 2004/099432), using an antibody raised against ITIH4 fragment 1 (discussed in more detail below), and spectra of polypeptides in the samples were generated by time-of-flight mass spectrometry on a Ciphergen PBSIIc or PCS4000 mass spectrometer. The spectra thus obtained were analyzed by Ciphergen Express™ Data Manager Software with Biomarker Wizard and Biomarker Pattern Software from Ciphergen Biosystems, Inc. The mass spectra for each group were subjected to scatter plot analysis. A Mann-Whitney test analysis was employed to compare ovarian cancer and control groups for each protein cluster in the scatter plot, and proteins were selected that differed significantly ($p<0.01$) between the two groups. This method is described in more detail in the Example Section.

Specific biomarkers thus discovered are presented in Table 1. The "ProteinChip assay" column refers to chromatographic fraction in which the biomarker is found, the type of biochip to which the biomarker binds and the wash conditions, as per the Examples. In each case, the biomarkers each may be found using a variety of alternate ProteinChip assays. The "theoretical mass" provides the expected mass based on amino acid sequence and modifications such as disulfide bonds.

TABLE 1

| Marker | P-Value | Up or down regulated in ovarian cancer | ProteinChip ® assay |
|---|---|---|---|
| Hepcidin-25 M2789 (theoretical mass = 2789.41 D) | 0.002 | Up | Urine, CM10, wash with 100 mM, sodium acetate, pH 4 |
| | 0.0011 | Up | Urine, IMAC30-$Cu^{++}$, wash with 100 mM sodium phosphate, 0.5 M NaCl, pH 7 |
| | 0.0000069 | Up | Serum, IMAC30-$Cu^{++}$, wash with 50 mM sodium phosphate buffer, 205 mM NaCl, pH 6.0 |
| | Sample set 1 discovery ovarian Cancer vs. control: 0.001040 ovarian Cancer vs. other cancers: 0.000002 | Up | Serum, immunoprecipitate ITIH4 (3272 m/z fragment), wash with PBS/0.1% Triton, elute with organic buffer, IMAC-$Cu^{++}$, wash with organic buffer |
| | Sample set 2 Validation 0.000007 | Up | Serum, immunoprecipitate ITIH4 (3272 m/z fragment), wash with PBS/0.1% Triton, elute with organic buffer, IMAC-$Cu^{++}$, wash with organic buffer |
| | Sample set 3 Validation 0.000000 | Up | Serum, immunoprecipitate ITIH4 (3272 m/z fragment), wash with PBS/0.1% Triton, elute with organic buffer, IMAC-$Cu^{++}$, wash with organic buffer |
| Hepcidin-24 M2673 (theoretical mass = 2674.32 D) | 0.001 | Up | Urine, CM10, wash with 100 mM sodium acetate, pH 4 |
| | 0.01 | Up | Urine, IMAC30-$Cu^{++}$, wash with 100 mM sodium phosphate, 0.5 M NaCl, pH 7 |
| | Sample set 1 discovery ovarian Cancer vs. control: 0.000009 ovarian Cancer vs. other cancer: 0.000002 | Up | Serum, immunoprecipitate ITIH4 (3272 m/z fragment), wash with PBS/0.1% Triton, elute with organic buffer, IMAC-$Cu^{++}$, wash with organic buffer |
| | Sample set 2 Validation 0.000097 | Up | Serum, immunoprecipitate ITIH4 (3272 m/z fragment), wash with PBS/0.1% Triton, elute with organic buffer, IMAC-$Cu^{++}$, wash with organic buffer |
| | Sample set 3 Validation 0.000001 | Up | Serum, immunoprecipitate ITIH4 (3272 m/z fragment), wash with PBS/0.1% Triton, elute with organic buffer, IMAC-$Cu^{++}$, wash with organic buffer |
| Hepcidin-22 M2436 (theoretical mass = 2436.07) | 0.0002 | Up | Urine, CM10, wash with 100 mM sodium acetate, pH 4 |
| | 0.0619 | Up | Urine, IMAC30-$Cu^{++}$, wash with 100 mM sodium phosphate, 0.5 M NaCl, pH 7 |
| | Sample set 1 discovery ovarian Cancer vs. control: 0.000030 ovarian Cancer vs. other cancer: 0.000015 | Up | Serum, immunoprecipitate ITIH4, wash with PBS/0.1% Triton, elute with organic buffer, IMAC-$Cu^{++}$, wash with organic buffer |
| | Sample set 2 Validation 0.002027 | Up | Serum, immunoprecipitate ITIH4 (3272 m/z fragment), wash with PBS/0.1% Triton, elute with organic buffer, IMAC-$Cu^{++}$, wash with organic buffer |
| | Sample set 3 Validation 0.000000 | Up | Serum, immunoprecipitate ITIH4 (3272 m/z fragment), wash with PBS/0.1% Triton, elute with organic buffer, IMAC-$Cu^{++}$, wash with organic buffer |
| Hepcidin-20 M2191 (theoretical mass = 2191.78) | 0.0061 | Up | Urine, CM10, wash with 100 mM sodium acetate, pH 4 |
| | 0.0023 | Up | Urine, IMAC30-$Cu^{++}$, wash with 100 mM sodium phosphate, 0.5 M NaCl, pH 7 |
| | Sample set 1 discovery ovarian | Up | Serum, immunoprecipitate ITIH4 (3272 m/z fragment), wash with PBS/0.1% Triton, |

TABLE 1-continued

| Marker | P-Value | Up or down regulated in ovarian cancer | ProteinChip ® assay |
|---|---|---|---|
| | Cancer vs. control: 0.000009 ovarian Cancer vs. other cancer: 0.000007 | | elute with organic buffer, IMAC-Cu++, wash with organic buffer |
| Sample set 2 Validation | 0.020419 | Up | Serum, immunoprecipitate ITIH4 (3272 m/z fragment), wash with PBS/0.1% Triton, elute with organic buffer, IMAC-Cu++, wash with organic buffer |
| Sample set 3 Validation | 0.000000 | Up | Serum, immunoprecipitate ITIH4 (3272 m/z fragment), wash with PBS/0.1% Triton, elute with organic buffer, IMAC-Cu++, wash with organic buffer |

The amino acid sequences of hepcidin-25, -24, -22 and -20 are:

```
Hepcidin-25 (SEQ ID NO: 13):
DTHFPICIFCCGCCHRSKCGMCCKT

Hepcidin-24 (SEQ ID NO: 14):
 THFPICIFCCGCCHRSKCGMCCKT

Hepcidin-22 (SEQ ID NO: 16):
   FPICIFCCGCCHRSKCGMCCKT

Hepcidin-20 (SEQ ID NO: 18):
     ICIFCCGCCHRSKCGMCCKT
```

The biomarkers of this invention are further characterized by their binding properties on chromatographic surfaces. Hepcidin binds to cation exchange adsorbents (e.g., the Ciphergen® CM10 ProteinChip® array) after washing with 100 mM sodium acetate at pH 4. Hepcidin also binds to metal chelate adsorbents (e.g., the Ciphergen® IMAC-Cu++ ProteinChip® array) after washing with 100 mM sodium phosphate, 0.5 M NaCl, pH 7 or organic buffer. Hepcidin may be visualized in the same assay as used to visualize ITIH4, as described below.

The preferred biological sources for detection of hepcidin is urine or serum. Hepcidin may also be detected in ascites fluid and cyst fluid, tissues and organs such as liver, and in specific cells, such as macrophages.

2.2. Transthyretin

Transthyretin, also called "pre-albumin" is another biomarker that is useful in the methods of the present invention. Transthyretin and variants thereof are described as biomarkers for ovarian cancer in US patent publication 2005-0059013 A1 and International Patent Publication WO 2005/098447. Unmodified transthyretin is a 127 amino acid protein deriving from a 147 amino acid precursor (SwissProt Accession No. P02766). The transthyretin biomarkers of the present invention include any or all of unmodified transthyretin and various modified forms. Transthyretin is recognized by antibodies available from, e.g., Dako (catalog A0002) (on the world wide web at dako.com, Glostrup, Denmark).

In mass spectra of serum, transthyretin appears as a cluster of peaks around 13.9 K Daltons. This cluster includes several forms of transthyretin including unmodified transthyretin, S-sulfonated thransthyretin, S-cysteinylated transthyretin, S-Gly-Cys transthyretin and S-glutathionylated transthryetin. Any and/or all of these is useful as a biomarker for ovarian cancer. However, the S-cysteinylated version represents the dominant form in the spectrum and is a preferred biomarker when using mass spectrometry. Another variant of transthyretin useful as a biomarker is transthyretin ΔN10. Specific transthyretin biomarkers thus discovered are presented in Table 2.

TABLE 2

| Marker | P-Value | Up or down regulated in ovarian cancer | ProteinChip ® assay |
|---|---|---|---|
| transthyretin ΔN10 (M12,870.9) (predicted mass 12,887 daltons) | p < 0.001 | Down (ovarian v. non-ovarian) | Q10 array using 100 mM Sodium Phosphate buffer, pH 7.0 (PB buffer) |
| unmodified transthyretin (M13900) (predicted mass 13,761 daltons) | p < 0.001 | Down (ovarian v. non-ovarian) | Q10 array using 100 mM Sodium Phosphate buffer, pH 7.0 (PB buffer) |
| sulfonated transthyretin (M13850) (predicted mass 13,841 daltons) | p < 0.001 | Down (ovarian v. non-ovarian) | Q10 array using 100 mM Sodium Phosphate buffer, pH 7.0 (PB buffer) |
| cysteinylated transthyretin (M13,890.8) (predicted mass 13,880 daltons) | p < 0.001 | Down (ovarian v. non-ovarian) | Q10 array using 100 mM Sodium Phosphate buffer, pH 7.0 (PB buffer) |
| CysGly modified transthyretin (M13944) (predicted mass 13,937 daltons) | p < 0.001 | Down (ovarian v. non-ovarian) | Q10 array using 100 mM Sodium Phosphate buffer, pH 7.0 (PB buffer) |
| glutathionylated transthyretin (M14,086.9) (predicted mass 14,066 daltons) | p < 0.001 | Down (ovarian v. non-ovarian) | Q10 array using 100 mM Sodium Phosphate buffer, pH 7.0 (PB buffer) |

2.3. ApoA1

Another biomarker that is useful in the methods of the present invention is apolipoprotein A1, also referred to as Apo A1. Apo A1 is described as a biomarker for ovarian cancer in US patent publication 2005-0059013 A1 and International Patent Publication WO 2005/098447. Apo A1 is a 243 amino acid protein derived from a 267 amino acid precursor (SwissProt Accession No. P02647). Apo A1 is recognized by antibodies available from, e.g., EMD Biosciences, Inc. (catalog 178474) (on the worldwide wed at emdbiosciences.com/home.asp, San Diego, Calif.). Specific Apo A1 biomarkers are presented in Table 3. Apo A1 can be visualized on H50 arrays or IMAC30 or IMAC50 arrays, but is preferentially visualized on H50 arrays. TABLE-US-00004 TABLE 3 Up or down regulated in Marker P-Value ovarian cancer ProteinChip .RTM. assay Apo A1<0.000001 Down H50 buffer (10% (M28043) acetonitrile, 0.1% TFA (predicted mass: IMAC Cu.sup.++ 28,078.62 D) Apo A1 variant Down H50 buffer (10% (M29977.4) acetonitrile, 0.1% TFA (appears as shoulder to peak at 28,043 D)

TABLE 3

| Marker | P-Value | Up or down regulated in ovarian cancer | ProteinChip ® assay |
|---|---|---|---|
| Apo A1 (M28043) (predicted mass: 28,078.62 D) | <.000001 | Down | H50 buffer (10% acetonitrile, 0.1% TFA IMAC $Cu^{++}$ |
| ApoA1 variant (M29977.4) (appears as shoulder to peak at 28,043 D) | | Down | H50 buffer (10% acetonitrile, 0.1% TFA |

Preferred methods of the present invention include the use of modified forms of Apo A1. Modification of Apo A1 may include the post-translational addition of various chemical groups, for example, glycosylation and lipidation.

2.4. Transferrin

Another biomarker that is useful in the methods of the present invention is transferrrin. Transferrrin is described as a biomarker for ovarian cancer in US patent publication 2005-0214760 A1. Transferrrin is a 679 amino acid protein derived from a 698 amino acid precursor (GenBank Accession No. NP.sub.-001054 GI:4557871; SwissProt Accesion No. P02787). Transferrrin is recognized by antibodies available from, e.g., Dako (catalog A006) (on the world wide web at dako.com, Glostrup, Denmark). Transferrin is glycosylated. Therefore, the measured molecular weight is higher than the theoretical weight, which does not take glycosylation into account. Specific transferrin biomarkers are presented in Table 4. TABLE-US-00005 TABLE 4 Up or down regulated in Marker P-Value ovarian cancer ProteinChip .RTM. assay transferrin <0.0001 Down IMAC-Ni (M79K) 100 mM Na.sub.2HPO4 pH 6.0 (predicted mass: IMAC-Cu 75,181 D) 50 mM Na phosphate 0.25M NaCI pH 6.0

TABLE 4

| Marker | P-Value | Up or down regulated in ovarian cancer | ProteinChip ® assay |
|---|---|---|---|
| transferrin (M79K) (predicted mass: 75,181 D) | <0.0001 | Down | IMAC-Ni 100 mM $Na_2HPO_4$ pH 6.0 IMAC-Cu 50 mM Na phosphate 0.25M NaCl pH 6.0 |

2.5. CTAP-III:

Another biomarker that is useful in the methods of the present invention is CTAP-III (connective tissue activating peptide III), derived from platelet basic protein. CTAP-III is described as a biomarker for ovarian cancer in U.S. provisional patent application 60/693,324, filed Jun. 22, 2005 (Zhang et al.). CTAP-III is an 85 amino acid protein (SwissProt P02775). CTAP-III is recognized by antibodies available from, e.g., Chemicon International (catalog 1484P) (on the worldwide web at chemicon.com, Temecula, Calif.) CTAP-III is a fragment of platelet basic protein and includes amino acids 44-128 of platelet basic protein. The specific CTAP-III biomarker is presented in Table 5. TABLE-US-00006 TABLE 5 Up or down regulated in Marker P-Value ovarian cancer ProteinChip .RTM. assay CTAP-III <0.0001 Up IMAC-Cu.sup.++ (M9290) 100 mM Na phosphate, (predicted mass: pH 7.0 9287.74 D).

TABLE 5

| Marker | P-Value | Up or down regulated in ovarian cancer | ProteinChip ® assay |
|---|---|---|---|
| CTAP-III (M9290) (predicted mass: 9287.74 D) | <0.0001 | Up | IMAC-$Cu^{++}$ 100 mM Na phosphate, pH 7.0 |

2.6 ITIH4 Fragment

Other biomarkers that are useful in the methods of the present invention one or more of a closely related set of cleavage fragments of inter-α-trypsin inhibitor heavy chain H4 precursor, also referred to alternatively herein as "ITIH4 fragments." ITIH4 fragments are described as biomarkers for ovarian cancer in US patent publication 2005-0059013 A1, International Patent Publication WO 2005/098447 and Fung et al., Int. J. Cancer 115:783-789 (2005). ITIH4 fragments can be selected from the group consisting of ITIH4 fragment no. 1, ITIH4 fragment no. 2, and ITIH4 fragment no. 3. Specific ITIH4 internal fragment biomarkers are presented in Table 6.

TABLE 6

| Marker | P-Value | Up or down regulated in ovarian cancer | ProteinChip ® assay |
|---|---|---|---|
| ITIH4 fragment 1 (M3272) (predicted mass: 3273.72 D) | <0.01 | Up | IMAC-$Cu^{++}$ 100 mM Na phosphate, pH 7.0 |
| ITIH4 fragment 2 (M2725) (predicted mass: 2725.06 D) | <0.02 | Up | IMAC-$Cu^{++}$ 100 mM Na phosphate, pH 7.0 |
| ITIH4 fragment 3 (M2627) (predicted mass: 2627.94 D) | <0.0057 | Up | IMAC-$Cu^{++}$ 100 mM Na phosphate, pH 7.0 |

The amino acid sequences of the ITIH4 fragments were determined to be:

```
ITIH4 fragment 1 (SEQ ID NO: 23):
MNFRPGVLSSRQLGLPGPPDVPDHAAYHPF

ITIH4 fragment 2 (SEQ ID NO: 24):
PGVLSSRQLGLPGPPDVPDHAAYHPF

ITIH4 fragment 3 (SEQ ID NO: 25):
GVLSSRQLGLPGPPDVPDHAAYHPF
```

ITIH4 precursor is a 930 amino acid protein (SwissProt Q14624). ITIH4 fragment 1 spans amino acids 658-687 of human ITIH4 precursor. ITIH4 fragment 2 spans amino acids 662-687 of ITIH4 precursor. ITIH4 fragment 3 spans amino acids 663-687 of ITIH4 precursor.

Additionally, preferred methods of the present invention include the use of modified forms of ITIH4 fragment. Modification of ITIH4 fragment may include the post-translational addition of various chemical groups, for example, glycosylation, lipidation, cysteinylation, and glutathionylation.

2.7. β-2 Microglobulin

Another biomarker that is useful in the methods of the present invention is .beta.2-microglobulin. .beta.2-microglobulin is described as a biomarker for ovarian cancer in U.S. provisional patent publication 60/693,679, filed Jun. 24, 2005

(Fung et al.). .beta.2-microglobulin is a 99 amino acid protein derived from an 119 amino acid precursor (GI: 179318; SwissProtAccession No. P61769). β2-microglobulin is recognized by antibodies available from, e.g., Abcam (catalog AB759) (on the worldwide web at abcam.com, Cambridge, Mass.). Specific β2-microglobulin biomarkers are presented in Table 7. TABLE-US-00009 TABLE 8 Up or down regulated in ProteinChip .RTM. Marker P-Value ovarian cancer assay β2-microglobulin <0.0001 Up IMAC-Cu.sup.++ (M11.7K) (predicted mass: 11729.17 D).

TABLE 8

| Marker | P-Value | Up or down regulated in ovarian cancer | ProteinChip ® assay |
|---|---|---|---|
| β2-microglobulin (M11.7K) (predicted mass: 11729.17 D) | <0.0001 | Up | IMAC-Cu$^{++}$ |

3. Biomarkers and Different Forms of A Protein

Proteins frequently exist in a sample in a plurality of different forms. These forms can result from either or both of pre- and post-translational modification. Pre-translational modified forms include allelic variants, splice variants and RNA editing forms. Post-translationally modified forms include forms resulting from proteolytic cleavage (e.g., fragments of a parent protein), glycosylation, phosphorylation, lipidation, oxidation, methylation, cysteinylation, sulphonation and acetylation. When detecting or measuring a protein in a sample, the ability to differentiate between different forms of a protein depends upon the nature of the difference and the method used to detect or measure. For example, an immunoassay using a monoclonal antibody will detect all forms of a protein containing the eptiope and will not distinguish between them. However, a sandwich immunoassay that uses two antibodies directed against different epitopes on a protein will detect all forms of the protein that contain both epitopes and will not detect those forms that contain only one of the epitopes. In diagnostic assays, the inability to distinguish different forms of a protein has little impact when the forms detected by the particular method used are equally good biomarkers as any particular form. However, when a particular form (or a subset of particular forms) of a protein is a better biomarker than the collection of different forms detected together by a particular method, the power of the assay may suffer. In this case, it is useful to employ an assay method that distinguishes between forms of a protein and that specifically detects and measures a desired form or forms of the protein. Distinguishing different forms of an analyte or specifically detecting a particular form of an analyte is referred to as "resolving" the analyte.

Mass spectrometry is a particularly powerful methodology to resolve different forms of a protein because the different forms typically have different masses that can be resolved by mass spectrometry. Accordingly, if one form of a protein is a superior biomarker for a disease than another form of the biomarker, mass spectrometry may be able to specifically detect and measure the useful form where traditional immunoassay fails to distinguish the forms and fails to specifically detect to useful biomarker.

One useful methodology combines mass spectrometry with immunoassay. First, a biosepcific capture reagent (e.g., an antibody, aptamer or Affibody that recognizes the biomarker and other forms of it) is used to capture the biomarker of interest. Preferably, the biospecific capture reagent is bound to a solid phase, such as a bead, a plate, a membrane or a chip.

After unbound materials are washed away, the captured analytes are detected and/or measured by mass spectrometry. (This method also will also result in the capture of protein interactors that are bound to the proteins or that are otherwise recognized by antibodies and that, themselves, can be biomarkers.) Various forms of mass spectrometry are useful for detecting the protein forms, including laser desorption approaches, such as traditional MALDI or SELDI, and electrospray ionization.

Thus, when reference is made herein to detecting a particular protein or to measuring the amount of a particular protein, it means detecting and measuring the protein with or without resolving various forms of protein. For example, the step of "measuring hepcidin" includes measuring hepcidin by means that do not differentiate between various forms of the protein (e.g., certain immunoassays) as well as by means that differentiate some forms from other forms or that measure a specific form of the protein (e.g., any and/or all of hepcidin-25, hepcidin-24, hepcidin-22 and hepcidin-20, individually or in combination). In contrast, when it is desired to measure a particular form or forms of a protein, e.g., a particular form of hepcidin, the particular form (or forms) is specified. For example, "measuring hepcidin-25" means measuring hepcidin-25 in a way that distinguishes it from other forms of hepcidin, e.g., hepcidin-24, hepcidin-22 and hepcidin-20. Similarly, reference to "measuring transthyretin" includes measuring any and/or all forms of transthyretin found in a subject test sample, individually or in combination, while reference to "measuring cysteinlyated transthyretin" means measuring transthryetin in a way that allows one to distinguish cysteinylated transthyretin from other forms of transthyretin found in a patient sample, e.g., transthyretin ΔN10, unmodified transthyretin, glutathionylated transthryetin, sulfonated transthryetin, etc. "Measuring un-cleaved transthyretin" means measuring any individual or combination of unmodified transthyretin, sulfonated transthryetin, cysteinylated transthyretin, CysGly modified transthyretin and glutathionylated transthryetin.

4. Detection of Biomarkers for Ovarian Cancer

The biomarkers of this invention can be detected by any suitable method. Detection paradigms include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

In one embodiment, a sample is analyzed by means of a biochip. A biochip generally comprises a solid substrate having a substantially planar surface, to which a capture reagent (also called an adsorbent or affinity reagent) is attached. Frequently, the surface of a biochip comprises a plurality of addressable locations, each of which has the capture reagent bound there.

Protein biochips are biochips adapted for the capture of polypeptides. Many protein biochips are described in the art. These include, for example, protein biochips produced by Ciphergen Biosystems, Inc. (Fremont, Calif.), Zyomyx (Hayward, Calif.), Invitrogen (Carlsbad, Calif.), Biacore (Uppsala, Sweden) and Procognia (Berkshire, UK). Examples of such protein biochips are described in the following patents or published patent applications: U.S. Pat. No. 6,225,047

(Hutchens & Yip); U.S. Pat. No. 6,537,749 (Kuimelis and Wagner); U.S. Pat. No. 6,329,209 (Wagner et al.); PCT International Publication No. WO 00/56934 (Englert et al.); PCT International Publication No. WO 03/048768 (Boutell et al.) and U.S. Pat. No. 5,242,828 (Bergstrom et al.).

4.1. Detection by Mass Spectrometry

In a preferred embodiment, the biomarkers of this invention are detected by mass spectrometry, a method that employs a mass spectrometer to detect gas phase ions. Examples of mass spectrometers are time-of-flight, magnetic sector, quadrupole filter, ion trap, ion cyclotron resonance, electrostatic sector analyzer and hybrids of these.

In a further preferred method, the mass spectrometer is a laser desorption/ionization mass spectrometer. In laser desorption/ionization mass spectrometry, the analytes are placed on the surface of a mass spectrometry probe, a device adapted to engage a probe interface of the mass spectrometer and to present an analyte to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer. The analyis of proteins by LDI can take the form of MALDI or of SELDI 4.1.1. Seldi A preferred mass spectrometric technique for use in the invention is "Surface Enhanced Laser Desorption and Ionization" or "SELDI," as described, for example, in U.S. Pat. No. 5,719,060 and No. 6,225,047, both to Hutchens and Yip. This refers to a method of desorption/ionization gas phase ion spectrometry (e.g., mass spectrometry) in which an analyte (here, one or more of the biomarkers) is captured on the surface of a SELDI mass spectrometry probe.

SELDI also has been called is called "affinity capture mass spectrometry" or "Surface-Enhanced Affinity Capture" ("SEAC"). This version involves the use of probes that have a material on the probe surface that captures analytes through a non-covalent affinity interaction (adsorption) between the material and the analyte. The material is variously called an "adsorbent," a "capture reagent," an "affinity reagent" or a "binding moiety." Such probes can be referred to as "affinity capture probes" and as having an "adsorbent surface." The capture reagent can be any material capable of binding an analyte. The capture reagent is attached to the probe surface by physisorption or chemisorption. In certain embodiments the probes have the capture reagent already attached to the surface. In other embodiments, the probes are pre-activated and include a reactive moiety that is capable of binding the capture reagent, e.g., through a reaction forming a covalent or coordinate covalent bond. Epoxide and acyl-imidizole are useful reactive moieties to covalently bind polypeptide capture reagents such as antibodies or cellular receptors. Nitrilotriacetic acid and iminodiacetic acid are useful reactive moieties that function as chelating agents to bind metal ions that interact non-covalently with histidine containing peptides. Adsorbents are generally classified as chromatographic adsorbents and biospecific adsorbents.

"Chromatographic adsorbent" refers to an adsorbent material typically used in chromatography. Chromatographic adsorbents include, for example, ion exchange materials, metal chelators (e.g., nitrilotriacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents).

"Biospecific adsorbent" refers to an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances, the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. Further examples of adsorbents for use in SELDI can be found in U.S. Pat. No. 6,225,047. A "bioselective adsorbent" refers to an adsorbent that binds to an analyte with an affinity of at least $10^{-8}$ M.

Protein biochips produced by Ciphergen Biosystems, Inc. comprise surfaces having chromatographic or biospecific adsorbents attached thereto at addressable locations. Ciphergen ProteinChip® arrays include NP20 (hydrophilic); H4 and H50 (hydrophobic); SAX-2, Q-10 and (anion exchange); WCX-2 and CM-10 (cation exchange); IMAC-3, IMAC-30 and IMAC-50 (metal chelate); and PS-10, PS-20 (reactive surface with acyl-imidizole, epoxide) and PG-20 (protein G coupled through acyl-imidizole). Hydrophobic ProteinChip arrays have isopropyl or nonylphenoxy-poly(ethylene glycol)methacrylate functionalities. Anion exchange ProteinChip arrays have quaternary ammonium functionalities. Cation exchange ProteinChip arrays have carboxylate functionalities. Immobilized metal chelate ProteinChip arrays have nitrilotriacetic acid functionalities (IMAC 3 and IMAC 30) or O-methacryloyl-N,N-bis-carboxymethyl tyrosine funtionalities (IMAC 50) that adsorb transition metal ions, such as copper, nickel, zinc, and gallium, by chelation. Preactivated ProteinChip arrays have acyl-imidizole or epoxide functional groups that can react with groups on proteins for covalent binding.

Such biochips are further described in: U.S. Pat. No. 6,579,719 (Hutchens and Yip, "Retentate Chromatography," Jun. 17, 2003); U.S. Pat. No. 6,897,072 (Rich et al., "Probes for a Gas Phase Ion Spectrometer," May 24, 2005); U.S. Pat. No. 6,555,813 (Beecher et al., "Sample Holder with Hydrophobic Coating for Gas Phase Mass Spectrometer," Apr. 29, 2003); U.S. Patent Publication No. U.S. 2003-0032043 A1 (Pohl and Papanu, "Latex Based Adsorbent Chip," Jul. 16, 2002); and PCT International Publication No. WO 03/040700 (Um et al., "Hydrophobic Surface Chip," May 15, 2003); U.S. Patent Publication No. US 2003-0218130 A1 (Boschetti et al., "Biochips With Surfaces Coated With Polysaccharide-Based Hydrogels," Apr. 14, 2003) and U.S. Patent Publication No. U.S. 2005-059086 A1 (Huang et al., "Photocrosslinked Hydrogel Blend Surface Coatings," Mar. 17, 2005).

In general, a probe with an adsorbent surface is contacted with the sample for a period of time sufficient to allow the biomarker or biomarkers that may be present in the sample to bind to the adsorbent. After an incubation period, the substrate is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. Unless the probe has both SEAC and SEND properties (as described herein), an energy absorbing molecule then is applied to the substrate with the bound biomarkers.

In yet another method, one can capture the biomarkers with a solid-phase bound immuno-adsorbent that has antibodies that bind the biomarkers. After washing the adsorbent to remove unbound material, the biomarkers are eluted from the solid phase and detected by applying to a SELDI chip that binds the biomarkers and analyzing by SELDI.

The biomarkers bound to the substrates are detected in a gas phase ion spectrometer such as a time-of-flight mass spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

4.1.2. Send

Another method of laser desorption mass spectrometry is called Surface-Enhanced Neat Desorption ("SEND"). SEND involves the use of probes comprising energy absorbing molecules that are chemically bound to the probe surface ("SEND probe"). The phrase "energy absorbing molecules" (EAM) denotes molecules that are capable of absorbing energy from a laser desorption/ionization source and, thereafter, contribute to desorption and ionization of analyte molecules in contact therewith. The EAM category includes molecules used in MALDI, frequently referred to as "matrix," and is exemplified by cinnamic acid derivatives, sinapinic acid (SPA), cyano-hydroxy-cinnamic acid (CHCA) and dihydroxybenzoic acid, ferulic acid, and hydroxyaceto-phenone derivatives. In certain embodiments, the energy absorbing molecule is incorporated into a linear or cross-linked polymer, e.g., a polymethacrylate. For example, the composition can be a co-polymer of α-cyano-4-methacryloyloxycinnamic acid and acrylate. In another embodiment, the composition is a co-polymer of α-cyano4-methacryloyloxycinnamic acid, acrylate and 3-(tri-ethoxy)silyl propyl methacrylate. In another embodiment, the composition is a co-polymer of α-cyano-4-methacryloyloxycinnamic acid and octadecylmethacrylate ("C18 SEND"). SEND is further described in U.S. Pat. No. 6,124,137 and PCT International Publication No. WO 03/64594 (Kitagawa, "Monomers And Polymers Having Energy Absorbing Moieties Of Use In Desorption/Ionization Of Analytes," Aug. 7, 2003).

SEAC/SEND is a version of laser desorption mass spectrometry in which both a capture reagent and an energy absorbing molecule are attached to the sample presenting surface. SEAC/SEND probes therefore allow the capture of analytes through affinity capture and ionization/desorption without the need to apply external matrix. The C18 SEND biochip is a version of SEAC/SEND, comprising a C18 moiety which functions as a capture reagent, and a CHCA moiety which functions as an energy absorbing moiety.

4.1.3. Separ

Another version of LDI is called Surface-Enhanced Photolabile Attachment and Release ("SEPAR"). SEPAR involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker profile, pursuant to the present invention.

4.1.4. Maldi

MALDI is a traditional method of laser desorption/ionization used to analyte biomolecules such as proteins and nucleic acids. In one MALDI method, the sample is mixed with matrix and deposited directly on a MALDI chip. However, the complexity of biological samples such as serum or urine make this method less than optimal without prior fractionation of the sample. Accordingly, in certain embodiments with biomarkers are preferably first captured with biospecific (e.g., an antibody) or chromatographic materials coupled to a solid support such as a resin (e.g., in a spin column). Specific affinity materials that bind the biomarkers of this invention are described above. After purification on the affinity material, the biomarkers are eluted and then detected by MALDI.

4.1.5. Other Forms of Ionization in Mass Spectrometry

In another method, the biomarkers are detected by LC-MS or LC-LC-MS. This involves resolving the proteins in a sample by one or two passes through liquid chromatography, followed by mass spectrometry analysis, typically electrospray ionization.

4.1.6. Data Analysis

Analysis of analytes by time-of-flight mass spectrometry generates a time-of-flight spectrum. The time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. In Ciphergen's ProteinChip® software, data processing typically includes TOF-to-M/Z transformation to generate a mass spectrum, baseline subtraction to eliminate instrument offsets and high frequency noise filtering to reduce high frequency noise.

Data generated by desorption and detection of biomarkers can be analyzed with the use of a programmable digital computer. The computer program analyzes the data to indicate the number of biomarkers detected, and optionally the strength of the signal and the determined molecular mass for each biomarker detected. Data analysis can include steps of determining signal strength of a biomarker and removing data deviating from a predetermined statistical distribution. For example, the observed peaks can be normalized, by calculating the height of each peak relative to some reference.

The computer can transform the resulting data into various formats for display. The standard spectrum can be displayed, but in one useful format only the peak height and mass information are retained from the spectrum view, yielding a cleaner image and enabling biomarkers with nearly identical molecular weights to be more easily seen. In another useful format, two or more spectra are compared, conveniently highlighting unique biomarkers and biomarkers that are up- or down-regulated between samples. Using any of these formats, one can readily determine whether a particular biomarker is present in a sample.

Analysis generally involves the identification of peaks in the spectrum that represent signal from an analyte. Peak selection can be done visually, but software is available, as part of Ciphergen's ProteinChip® software package, that can automate the detection of peaks. In general, this software functions by identifying signals having a signal-to-noise ratio above a selected threshold and labeling the mass of the peak at the centroid of the peak signal. In one useful application, many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Software used to analyze the data can include code that applies an algorithm to the analysis of the signal to determine whether the signal represents a peak in a signal that corresponds to a biomarker according to the present invention. The software also can subject the data regarding observed biomarker peaks to classification tree or ANN analysis, to determine whether a biomarker peak or combination of biomarker peaks is present that indicates the status of the particular clinical parameter under examination. Analysis of the data may be "keyed" to a variety of parameters that are obtained, either directly or indirectly, from the mass spectrometric analysis of the sample. These parameters include, but are not limited to, the presence or absence of one or more peaks, the shape of a peak or group of peaks, the height of one or more peaks, the log of the height of one or more peaks, and other arithmetic manipulations of peak height data.

4.1.7. General Protocol for SELDI Detection of Biomarkers for Ovarian Cancer

A preferred protocol for the detection of the biomarkers of this invention is as follows. The biological sample to be tested, e.g., serum, preferably is subject to pre-fractionation before SELDI analysis. This simplifies the sample and improves sensitivity. A preferred method of pre-fractionation involves contacting the sample with an anion exchange chromatographic material, such as Q HyperD (BioSepra, SA). The bound materials are then subject to stepwise pH elution using buffers at pH 9, pH 7, pH 5 and pH 4. (The fractions in which the biomarkers are eluted also is indicated in Table 1.) Various fractions containing the biomarker are collected.

The sample to be tested (preferably pre-fractionated) is then contacted with an affinity capture probe comprising an cation exchange adsorbent (preferably a CM10 ProteinChip array (Ciphergen Biosystems, Inc.)) or an IMAC adsorbent (preferably an IMAC30 ProteinChip array (Ciphergen Biosystems, Inc.)), again as indicated in Table 1. The probe is washed with a buffer that will retain the biomarker while washing away unbound molecules. A suitable wash for each biomarker is the buffer identified in Table 1. The biomarkers are detected by laser desorption/ionization mass spectrometry.

Alternatively, samples may be diluted, with or without denaturing, in the appropriate array binding buffer and bound and washed under conditions optimized for detecting each analyte.

ApoA1 Chromatographic Assay Performed on Tecan Aquarius-96:
1. Denature serum: add 7.5 ul 9M urea 2% CHAPS 50 mM Tris HCl pH9 to 5 ul of human serum, and mix at room temperature for 20 min. Dilute 1:400 with a solution containing: H50 buffer (10% acetonitrile, 0.1% TFA), and 0.12 mg/ml E. coli lysate.
2. Pre-activate H50 arrays: wash each well of the BioProcessor with 50% acetonitrile per well. Incubate at room temp for 5 min. Remove solution. Equilibrate with 150 μl H50 wash buffer (10% acetonitrile/0.1% TFA) two times for 5 minutes each. Remove buffer.
3. Add 50 ul of 1:400 diluted serum sample to each well. Incubate at room temp for 120 min.
4. Wash arrays 4 times with 150 ul of H50 buffer. Wash arrays with 150 ul of water 1 time.
5. Remove BioProcessor top. Air dry for 10 minutes.
6. Using a BioDot, add 0.75 ul of sinapinic acid matrix (SPA, Ciphergen, 12.5 mg/ml in 50% acetonitrile/0.5% TFA/0.1% TX100) per spot. Air day for 10 min in the BioDot chamber. Apply additional 0.75 ul SPA solution per spot. Air dry for 30 min in the chamber before reading arrays on PCS4000.
7. Read on PCS 4000, with focus mass at 28,000 Da, collect 10 shots per partition for a total of 530 shots per spot.

Transthyretin Chromatographic Assay Performed on Tecan Aquarius-96:
1. Sample dilution: 1:250 dilution of serum sample in a solution containing: 100 mM Sodium Phosphate buffer, pH 7.0 (PB buffer) with addition of 0.05 mg/ml E. coli lysate. Mix well.
2. Pre-treat Q10 arrays with the PB buffer, incubate 5 minutes. Remove buffer. Repeat once.
3. Add 50 ul of 1:250 diluted serum sample to each well and incubate for 120 min at room temp. Remove samples.
4. Wash arrays 4 times with 150 ul of PB buffer. Remove buffer after each wash.
5. Wash arrays with 150 ul of water one time. Remove water.
6. Remove BioProcessor. Air dry arrays for 30 minutes.
7. Using a BioDot, add 0.75 ul of sinapinic acid matrix (SPA, Ciphergen, 12.5 mg/ml in 50% acetonitrile/0.5% TFA) per spot. Air day for 10 min in the BioDot chamber. Apply additional 0.75 ul SPA solution per spot. Air dry for 30 min in the chamber before reading arrays on PCS4000.
8. Read on PCS 4000, with focus mass at 14,000 Da, collect 10 shots per partition for a total of 530 shots per spot.

ITIH4 Chromatograhic Assay Performed on Tecan Aquarius-96:
1. Sample dilution: 1:50 dilution of serum sample in IMAC binding/washing buffer (50 mM Na phosphate 0.25M NaCl pH 6.0). Mix well.
2. Pre-activate IMAC50 arrays: add 50 mM CuSO4 per well in a BioProcessor. Incubate at room temp for 10 min. Remove copper solution. Wash with water 4 times. Equilibrate IMAC50 arrays twice with the binding buffer.
3. Add 50 ul of 1:50 diluted serum sample to each well and incubate for 120 min at room temp. Remove samples.
4. Wash arrays 3 times with 150 ul of IMAC binding/washing buffer. Remove buffer after each wash.
5. Wash arrays with 150 ul of water 2 times. Remove water.
6. Remove BioProcessor. Air dry arrays for 30 minutes.
7. Using a BioDot, add 0.75 ul of sinapinic acid matrix (SPA, Ciphergen, 12.5 mg/ml in 50% acetonitrile/0.5% TFA) per spot. Air day for 10 min in the BioDot chamber. Apply additional 0.75 ul SPA solution per spot. Air dry for 30 min in the chamber before reading arrays on PCS4000.
8. Read on PCS 4000, with focus mass at 3,273 Da, collect 10 shots per partition for a total of 530 shots per spot.

Alternatively, if antibodies that recognize the biomarker are available, for example from Dako, U.S. Biological, Chemicon, Abcam and Genway. These can be attached to the surface of a probe, such as a pre-activated PS10 or PS20 ProteinChip array (Ciphergen Biosystems, Inc.). These antibodies can capture the biomarkers from a sample onto the probe surface. Then the biomarkers can be detected by, e.g., laser desorption/ionization mass spectrometry.

Any robot that performs fluidics operations can be used in these assays, for example, those available from Hewlett Packard and Hamilton.

4.2. Detection by Immunoassay

In another embodiment of the invention, the biomarkers of the invention are measured by a method other than mass spectrometry or other than methods that rely on a measurement of the mass of the biomarker. In one such embodiment that does not rely on mass, the biomarkers of this invention are measured by immunoassay. Immunoassay requires biospecific capture reagents, such as antibodies, to capture the biomarkers. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well known in the art.

This invention contemplates traditional immunoassays including, for example, sandwich immunoassays including ELISA or fluorescence-based immunoassays, as well as other enzyme immunoassays. Nephelometry is an assay done in liquid phase, in which antibodies are in solution. Binding of the antigen to the antibody results in changes in absorbance, which is measured. In the SELDI-based immunoassay, a biospecific capture reagent for the biomarker is attached to the surface of an MS probe, such as a pre-activated ProteinChip array. The biomarker is then specifically captured on the biochip through this reagent, and the captured biomarker is detected by mass spectrometry.

5. Determination of Subject Ovarian Cancer Status

The biomarkers of the invention can be used in diagnostic tests to assess ovarian cancer status in a subject, e.g., to diagnose ovarian cancer. The phrase "ovarian cancer status" includes any distinguishable manifestation of the disease, including non-disease. For example, ovarian cancer status includes, without limitation, the presence or absence of disease (e.g., ovarian cancer v. non-ovarian cancer), the risk of developing disease, the stage of the disease, the progression of disease (e.g., progress of disease or remission of disease over time) and the effectiveness or response to treatment of disease.

The correlation of test results with ovarian cancer status involves applying a classification algorithm of some kind to the results to generate the status. The classification algorithm may be as simple as determining whether or not the amount of hepcidin measured is above or below a particular cut-off number. When multiple biomarkers are used, the classification algorithm may be a linear regression formula. Alternatively, the classification algorithm may be the product of any of a number of learning algorithms described herein.

In the case of complex classification algorithms, it may be necessary to perform the algorithm on the data, thereby determining the classification, using a computer, e.g., a programmable digital computer. In either case, one can then record the status on tangible medium, for example, in computer-readable format such as a memory drive or disk or simply printed on paper. The result also could be reported on a computer screen.

5.1. Single Markers

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

The biomarkers of this invention show a statistical difference in different ovarian cancer statuses. Diagnostic tests that use these biomarkers alone or in combination show a sensitivity and specificity of at least 75%, at least 80%, at least 85%, at least 90%, at least 95%, at least 98% and about 100%.

Each biomarker listed in Table 1 is differentially present in ovarian cancer, and, therefore, each is individually useful in aiding in the determination of ovarian cancer status. The method involves, first, measuring the selected biomarker in a subject sample using the methods described herein, e.g., capture on a SELDI biochip followed by detection by mass spectrometry and, second, comparing the measurement with a diagnostic amount or cut-off that distinguishes a positive ovarian cancer status from a negative ovarian cancer status. The diagnostic amount represents a measured amount of a biomarker above which or below which a subject is classified as having a particular ovarian cancer status. For example, because hepcidin is up-regulated in ovarian cancer compared to normal, then a measured amount of hepcidin above the diagnostic cutoff provides a diagnosis of ovarian cancer. As is well understood in the art, by adjusting the particular diagnostic cut-off used in an assay, one can increase sensitivity or specificity of the diagnostic assay depending on the preference of the diagnostician. The particular diagnostic cut-off can be determined, for example, by measuring the amount of the biomarker in a statistically significant number of samples from subjects with the different ovarian cancer statuses, as was done here, and drawing the cut-off to suit the diagnostician's desired levels of specificity and sensitivity.

5.2. Combinations of Markers

While individual biomarkers are useful diagnostic biomarkers, it has been found that a combination of biomarkers can provide greater predictive value of a particular status than single biomarkers alone. Specifically, the detection of a plurality of biomarkers in a sample can increase the sensitivity and/or specificity of the test. A combination of at least two biomarkers is sometimes referred to as a "biomarker profile" or "biomarker fingerprint." Accordingly, hepcidin can be combined with other biomarkers for ovarian or endometrial cancer to improve the sensitivity and/or specificity of the diagnostic test.

In particular, it has been found that a diagnostic test for ovarian cancer status involving the measurement of both hepcidin and transthyretin has greater predictive power than the measurement of hepcidin alone. As indicated, hepcidin levels are increased in ovarian cancer and transthyretin levels are decreased. It further has been found that a diagnostic test combining at least three biomarkers or, in certain instances, seven biomarkers, provides greater predictive power than the measurement of both hepcidin and transthyretin. More specifically, it is contemplated that a diagnostic test for ovarian cancer status will include measuring hepcidin, transthyretin and at least one of Apo A1, transferrin, CTAP-III and ITIH4 fragment, and correlating these measurements with ovarian cancer status. It is also contemplated that $\beta$2-microglobulin could be combined with hepcidin and transthyretin, along with any of the four aforementioned biomarkers.

In a study on samples of a Japanese cohort, the combination of hepcidin, ApoA1, $\beta$2 microglobulin and CTAP-III was found to be a particularly effective diagnostic combination.

The diagnosis of ovarian cancer typically involves the measurement of CA125, as increased levels of this marker are correlated with ovarian cancer. Therefore, levels of CA125 can be correlated with any combination of the above markers in determining ovarian cancer status.

Other biomarkers with which hepcidin can be combined include, but are not limited to, CA125, CA125 II, CA15-3, CA19-9, CA72-4, CA 195, tumor associated trypsin inhibitor (TATI), CEA, placental alkaline phosphatase (PLAP), Sialyl TN, galactosyltransferase, macrophage colony stimulating factor (M-CSF, CSF-1), lysophosphatidic acid (LPA), 110 kD component of the extracellular domain of the epidermal growth factor receptor (p110EGFR), tissue kallikreins, e.g., kallikrein 6 and kallikrein 10 (NES-1), prostasin, HE4, creatine kinase B (CKB), LASA, HER-2/neu, urinary gonadotropin peptide, Dianon NB 70/K, Tissue peptide antigen (TPA), osteopontin, and haptoglobin, leptin, prolactin, insulin like growth factor I or II. CA125 is especially useful in that women undergoing tests for ovarian cancer typically have CA125 tested as routine part of the work-up.

5.3. Ovarian Cancer Status

Determining ovarian cancer status typically involves classifying an individual into one of two or more groups (statuses) based on the results of the diagnostic test. The diagnostic tests described herein can be used to classify between a number of different states.

5.3.1. Presence of Disease

In one embodiment, this invention provides methods for determining the presence or absence of ovarian cancer in a subject (status: ovarian cancer v. non-ovarian cancer). The presence or absence of ovarian cancer is determined by measuring the relevant biomarker or biomarkers and then either submitting them to a classification algorithm or comparing them with a reference amount and/or pattern of biomarkers that is associated with the particular risk level.

5.3.2. Determining Risk of Developing Disease

In one embodiment, this invention provides methods for determining the risk of developing ovarian cancer in a subject (status: low-risk v. high risk). Biomarker amounts or patterns are characteristic of various risk states, e.g., high, medium or low. The risk of developing a disease is determined by measuring the relevant biomarker or biomarkers and then either submitting them to a classification algorithm or comparing them with a reference amount and/or pattern of biomarkers that is associated with the particular risk level

5.3.3. Determining Stage of Disease

In one embodiment, this invention provides methods for determining the stage of disease in a subject. Each stage of the disease has a characteristic amount of a biomarker or relative amounts of a set of biomarkers (a pattern). The stage of a disease is determined by measuring the relevant biomarker or biomarkers and then either submitting them to a classification algorithm or comparing them with a reference amount and/or pattern of biomarkers that is associated with the particular stage. For example, one can classify between early stage ovarian cancer and non-ovarian cancer or among stage I ovarian cancer, stage II ovarian cancer and stage III ovarian cancer.

5.3.4. Determining Course (Progression/Remission) of Disease

In one embodiment, this invention provides methods for determining the course of disease in a subject. Disease course refers to changes in disease status over time, including disease progression (worsening) and disease regression (improvement). Over time, the amounts or relative amounts (e.g., the pattern) of the biomarkers changes. For example, hepcidin is increased with disease, while transthryetin is decreased in disease. Therefore, the trend of these markers, either increased or decreased over time toward diseased or non-diseased indicates the course of the disease. Accordingly, this method involves measuring one or more biomarkers in a subject for at least two different time points, e.g., a first time and a second time, and comparing the change in amounts, if any. The course of disease is determined based on these comparisons.

5.4. Reporting the Status

Additional embodiments of the invention relate to the communication of assay results or diagnoses or both to technicians, physicians or patients, for example. In certain embodiments, computers will be used to communicate assay results or diagnoses or both to interested parties, e.g., physicians and their patients. In some embodiments, the assays will be performed or the assay results analyzed in a country or jurisdiction which differs from the country or jurisdiction to which the results or diagnoses are communicated.

In a preferred embodiment of the invention, a diagnosis based on the differential presence in a test subject of any the biomarkers of Table 1 is communicated to the subject as soon as possible after the diagnosis is obtained. The diagnosis may be communicated to the subject by the subject's treating physician. Alternatively, the diagnosis may be sent to a test subject by email or communicated to the subject by phone. A computer may be used to communicate the diagnosis by email or phone. In certain embodiments, the message containing results of a diagnostic test may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

5.5. Subject Management

In certain embodiments of the methods of qualifying ovarian cancer status, the methods further comprise managing subject treatment based on the status. Such management includes the actions of the physician or clinician subsequent to determining ovarian cancer status. For example, if a physician makes a diagnosis of ovarian cancer, then a certain regime of treatment, such as prescription or administration of chemotherapy might follow. Alternatively, a diagnosis of non-ovarian cancer or non-ovarian cancer might be followed with further testing to determine a specific disease that might the patient might be suffering from. Also, if the diagnostic test gives an inconclusive result on ovarian cancer status, further tests may be called for.

6. Generation of Classification Algorithms for Qualifying Ovarian Cancer Status In some embodiments, data derived from the spectra (e.g., mass spectra or time-of-flight spectra) that are generated using samples such as "known samples" can then be used to "train" a classification model. A "known sample" is a sample that has been pre-classified. The data that are derived from the spectra and are used to form the classification model can be referred to as a "training data set." Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., diseased versus non-diseased).

The training data set that is used to form the classification model may comprise raw data or pre-processed data. In some embodiments, raw data can be obtained directly from time-of-flight spectra or mass spectra, and then may be optionally "pre-processed" as described above.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", *IEEE Transactions on Pattern Analysis and Machine Intelligence*, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (support vector machines).

A preferred supervised classification method is a recursive partitioning process. Recursive partitioning processes use recursive partitioning trees to classify spectra derived from unknown samples. Further details about recursive partitioning processes are provided in U.S. Pat. No. 6,675,104 (Paulse et al., "Method for analyzing mass spectra").

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use Thereof"S), U.S. Patent Application No. 2002 0193950 A1 (Gavin et al., "Method or analyzing mass spectra"), U.S. Patent Application No. 2003 0004402 A1 (Hitt et al., "Process for discriminating between biological states based on hidden patterns from biological data"), and U.S. Patent Application No. 2003 0055615 A1 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows™ or Linux™ based operating system. The digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

The learning algorithms described above are useful both for developing classification algorithms for the biomarkers already discovered, or for finding new biomarkers for ovarian cancer. The classification algorithms, in turn, form the base for diagnostic tests by providing diagnostic values (e.g., cut-off points) for biomarkers used singly or in combination.

A logistical regression analysis was performed on data generated from the experiments described in Example 4, below (smaller sample set). The analysis generated a classification algorithm to distinguish ovarian cancer from non-ovarian cancer based on seven biomarkers: hepcidin, ITIH4 fragment 1, CTAP-III, transthyretin, transferrin, beta-2 microglobulin and Apo-A1. The algorithm involved two steps. In the first step a number was generated from a test sample based on the following formula:

$$\text{Logit} = -1.673 + 0.7349*\text{hepc} - 0.6252*\text{ITIH4conc} + 0.1458*\text{CTAP-III2} - 0.4923*\text{Ttconc} - 0.5023*\text{TFR} - 0.1595*\text{M2B} + 0.0265*\text{Apo A1conc}$$

The measurements represented either normalized peak intensity or analyte concentration (designated "conc"). In the second step, the probability that a sample came from a subject having ovarian cancer was determined by the formula: $e^{Logit}/(1+e^{Logit})$. A cut-off is then applied based on the desired sensitivity or specificity of the test. The higher the cut-off number, the better the sensitivity of the assay. The specific numbers used in this assay depend upon the assay conditions and instrument used, and need to be re-calibrated whenever an assay is set up.

7. Compositions of Matter

In another aspect, this invention provides compositions of matter based on the biomarkers of this invention.

In one embodiment, this invention provides biomarkers of this invention in purified form. Purified biomarkers have utility as antigens to raise antibodies. Purified biomarkers also have utility as standards in assay procedures. As used herein, a "purified biomarker" is a biomarker that has been isolated from other proteins and peptdies, and/or other material from the biological sample in which the biomarker is found. The biomarkers can be isolated from biological fluids, such as urine or serum. Biomarkers may be purified using any method known in the art, including, but not limited to, mechanical separation (e.g., centrifugation), ammonium sulphate precipitation, dialysis (including size-exclusion dialysis), electrophoresis (e.g. acrylamide gel electrophoresis) size-exclusion chromatography, affinity chromatography, anion-exchange chromatography, cation-exchange chromatography, and methal-chelate chromatography. Such methods may be performed at any appropriate scale, for example, in a chromatography column, or on a biochip.

In another embodiment, this invention provides a biospecific capture reagent, optionally in purified form, that specifically binds a biomarker of this invention. In one embodiment, the biospecific capture reagent is an antibody. Such compositions are useful for detecting the biomarker in a detection assay, e.g., for diagnostics.

In another embodiment, this invention provides an article comprising a biospecific capture reagent that binds a biomarker of this invention, wherein the reagent is bound to a solid phase. For example, this invention contemplates a device comprising bead, chip, membrane, monolith or microtiter plate derivatized with the biospecific capture reagent. Such articles are useful in biomarker detection assays.

In another aspect this invention provides a composition comprising a biospecific capture reagent, such as an antibody, bound to a biomarker of this invention, the composition optionally being in purified form. Such compositions are useful for purifying the biomarker or in assays for detecting the biomarker.

In another embodiment, this invention provides an article comprising a solid substrate to which is attached an adsorbent, e.g., a chromatographic adsorbent or a biospecific capture reagent, to which is further bound a biomarker of this invention. In one embodiment, the article is a biochip or a probe for mass spectrometry, e.g., a SELDI probe. Such articles are useful for purifying the biomarker or detecting the biomarker.

8. Kits for Detection of Biomarkers for Ovarian Cancer

In another aspect, the present invention provides kits for qualifying ovarian cancer status, which kits are used to detect biomarkers according to the invention. In one embodiment, the kit comprises a solid support, such as a chip, a microtiter plate or a bead or resin having a capture reagent attached thereon, wherein the capture reagent binds a biomarker of the invention. Thus, for example, the kits of the present invention can comprise mass spectrometry probes for SELDI, such as ProteinChip® arrays. In the case of biospecfic capture reagents, the kit can comprise a solid support with a reactive surface, and a container comprising the biospecific capture reagent.

The kit can also comprise a washing solution or instructions for making a washing solution, in which the combination of the capture reagent and the washing solution allows capture of the biomarker or biomarkers on the solid support for subsequent detection by, e.g., mass spectrometry. The kit may include more than type of adsorbent, each present on a different solid support.

In a further embodiment, such a kit can comprise instructions for suitable operational parameters in the form of a label or separate insert. For example, the instructions may inform a consumer about how to collect the sample, how to wash the probe or the particular biomarkers to be detected.

In yet another embodiment, the kit can comprise one or more containers with biomarker samples, to be used as standard(s) for calibration.

9. Determining Therapeutic Efficacy of Pharmaceutical Drug

In another embodiment, this invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern or profile) of the biomarkers of this invention changes toward a non-disease profile. For example, hepcidin is increased with disease, while transthyretin is decreased in disease. Therefore, one can follow the course of the amounts of these biomarkers in the subject during the course of treatment. Accordingly, this method involves measuring one or more biomarkers in a subject receiving drug therapy, and correlating the amounts of the biomarkers with the disease status of the subject. One embodiment of this method involves determining the levels of the biomarkers for at least two different time points during a course of drug therapy, e.g., a first time and a second time, and comparing the change in amounts of the biomarkers, if any. For example, the biomarkers can be measured before and after drug administration or at two different time points during drug administration. The effect of therapy is determined based on these comparisons. If a treatment is effective, then the biomarkers will trend toward normal, while if treatment is ineffective, the biomarkers will trend toward disease indications. If a treatment is effective, then the biomarkers will trend toward normal, while if treatment is ineffective, the biomarkers will trend toward disease indications.

10. Use of Biomarkers for Ovarian Cancer in Screening Assays and Methods of Treating Ovarian Cancer The methods of the present invention have other applications as well. For example, the biomarkers can be used to screen for compounds that modulate the expression of the biomarkers in vitro or in vivo, which compounds in turn may be useful in treating or preventing ovarian cancer in patients. In another example, the biomarkers can be used to monitor the response to treatments for ovarian cancer. In yet another example, the biomarkers can be used in heredity studies to determine if the subject is at risk for developing ovarian cancer.

Compounds suitable for therapeutic testing may be screened initially by identifying compounds which interact with hepcidin and one or more biomarkers listed herein. By way of example, screening might include recombinantly expressing a biomarker, purifying the biomarker, and affixing the biomarker to a substrate. Test compounds would then be contacted with the substrate, typically in aqueous conditions, and interactions between the test compound and the biomarker are measured, for example, by measuring elution rates as a function of salt concentration. Certain proteins may recognize and cleave one or more biomarkers of Table I, in which case the proteins may be detected by monitoring the digestion of one or more biomarkers in a standard assay, e.g., by gel electrophoresis of the proteins.

In a related embodiment, the ability of a test compound to inhibit the activity of one or more of the biomarkers may be measured. One of skill in the art will recognize that the techniques used to measure the activity of a particular biomarker will vary depending on the function and properties of the biomarker. For example, an enzymatic activity of a biomarker may be assayed provided that an appropriate substrate is available and provided that the concentration of the substrate or the appearance of the reaction product is readily measurable. The ability of potentially therapeutic test compounds to inhibit or enhance the activity of a given biomarker may be determined by measuring the rates of catalysis in the presence or absence of the test compounds. The ability of a test compound to interfere with a non-enzymatic (e.g., structural) function or activity of hepcidin or another one or more of the biomarkers herein may also be measured. For example, the self-assembly of a multi-protein complex which includes hepcidin may be monitored by spectroscopy in the presence or absence of a test compound. Alternatively, if the biomarker is a non-enzymatic enhancer of transcription, test compounds which interfere with the ability of the biomarker to enhance transcription may be identified by measuring the levels of biomarker-dependent transcription in vivo or in vitro in the presence and absence of the test compound.

Test compounds capable of modulating the activity of any of the biomarkers of Table I may be administered to patients who are suffering from or are at risk of developing ovarian cancer or other cancer. For example, the administration of a test compound which increases the activity of a particular biomarker may decrease the risk of ovarian cancer in a patient if the activity of the particular biomarker in vivo prevents the accumulation of proteins for ovarian cancer. Conversely, the administration of a test compound which decreases the activity of a particular biomarker may decrease the risk of ovarian cancer in a patient if the increased activity of the biomarker is responsible, at least in part, for the onset of ovarian cancer.

In an additional aspect, the invention provides a method for identifying compounds useful for the treatment of disorders such as ovarian cancer which are associated with increased levels of modified forms of hepcidin. For example, in one embodiment, cell extracts or expression libraries may be screened for compounds which catalyze the cleavage of full-length hepcidin to form truncated forms of hepcidin. In one embodiment of such a screening assay, cleavage of hepcidin may be detected by attaching a fluorophore to hepcidin which remains quenched when hepcidin is uncleaved but which fluoresces when the protein is cleaved. Alternatively, a version of full-length hepcidin modified so as to render the amide bond between amino acids x and y uncleavable may be used to selectively bind or "trap" the cellular protesase which cleaves full-length hepcidin at that site in vivo. Methods for screening and identifying proteases and their targets are well-documented in the scientific literature, e.g., in Lopez-Ottin et al. (Nature Reviews, 3:509-519 (2002)).

In yet another embodiment, the invention provides a method for treating or reducing the progression or likelihood of a disease, e.g., ovarian cancer, which is associated with the increased levels of truncated hepcidin. For example, after one or more proteins have been identified which cleave full-length hepcidin, combinatorial libraries may be screened for compounds which inhibit the cleavage activity of the identified proteins. Methods of screening chemical libraries for such compounds are well-known in art. See, e.g., Lopez-Otin et al. (2002). Alternatively, inhibitory compounds may be intelligently designed based on the structure of hepcidin.

Full-length hepcidin is believed to be involved in regulation of the body's iron stores, as well as in hereditary hemochromatosis, chronic renal insufficiency, and renal anemia. Hepcidin expression is also induced as part of the body's immune response via the interleuking cascade. Because hepcidin is highly processed from its pre-pro and pro-forms, it is likely that there are proteases which target and cleave it. Therefore, in a further embodiment, the invention provides methods for identifying compounds which increase the affinity of truncated hepcidin for its target proteases. For example, compounds may be screened for their ability to cleave hepcidin. Test compounds capable of modulating the cleavage of hepcidin or the activity of molecules which interact with hepcidin may then be tested in vivo for their ability to slow or stop the progression of ovarian and/or endometrial cancer in a subject.

At the clinical level, screening a test compound includes obtaining samples from test subjects before and after the subjects have been exposed to a test compound. The levels in the samples of one or more of the biomarkers listed in Table I may be measured and analyzed to determine whether the levels of the biomarkers change after exposure to a test compound. The samples may be analyzed by mass spectrometry, as described herein, or the samples may be analyzed by any appropriate means known to one of skill in the art. For example, the levels of one or more of the biomarkers listed in Table I may be measured directly by Western blot using radio- or fluorescently-labeled antibodies which specifically bind to the biomarkers. Alternatively, changes in the levels of mRNA encoding the one or more biomarkers may be measured and correlated with the administration of a given test compound to a subject. In a further embodiment, the changes in the level of expression of one or more of the biomarkers may be measured using in vitro methods and materials. For example, human tissue cultured cells which express, or are capable of expressing, one or more of the biomarkers of Table I may be contacted with test compounds. Subjects who have been treated with test compounds will be routinely examined for any physiological effects which may result from the treatment. In particular, the test compounds will be evaluated for their ability to decrease disease likelihood in a subject. Alternatively, if the test compounds are administered to subjects who have previously been diagnosed with ovarian cancer, test compounds will be screened for their ability to slow or stop the progression of the disease.

11. EXAMPLES

11.1. Example 1

Discovery of Biomarkers for Ovarian Cancer

It is understood that the examples and embodiments described herein are for illustrative purposes only and that various modifications or changes in light thereof will be suggested to persons skilled in the art and are to be included within the spirit and purview of this application and scope of the appended claims.

Samples: Serum and urine samples were acquired from the MDACC Ovarian cancer sample bank (MD Anderson). The samples had been collected from cancer patients pre-operatively from years 2000 to 2004 and stored at −80° C. Sample distribution was as follows: ovarian cancer (OvCa), 200; endometrial cancer, 50; cervical cancer, 50 and benign, 50. Many, but not all, of the OvCa and benign serum and urine samples were from the same patient. The samples were run in two sets. The first set comprised the 200 ovarian cancer samples and 50 benign samples. This provided an initial list of candidate biomarkers. To test the tumor-type specificity of these candidate biomarkers, a subset (50) of ovarian cancer samples, along with the 50 benign samples, and the 50 endometrial and 50 cervical cancer samples were analyzed.

Serum Profiling: Serum profiling was performed only on the ovarian cancer and benign samples. Randomized templates containing the samples to be profiled were generated using the Ciphergen Express software program. Samples from the tumor bank were thawed on ice, added to a 96 well plate (following the template for arrangement), and centrifuged for 20 minutes at 4000 rpm. Aliquots of the serum were then put into fresh 96 well plates and stored at −80° C. until use. Serum samples were profiled on IMAC-$Cu^{++}$ and on Q10 (see protocol below) on triplicate ProteinChip Arrays. All replicates were prepared on the same day and were read on a PBSIIc (beginning the morning following preparation) and/ or a PCS4000 (beginning a few days after preparation). Arrays were processed with sample using a Biomek 2000 robot.

IMAC-Cu serum profiling Protocol: Serum was first denatured by a urea treatment. 5 μl serum was added to 7.5 μl 9M urea 2% CHAPS 50 mM Tris HCl pH 9 in a 96-well v-plate. The plate was covered with tape and shaken at Rm T for 20 minutes. 237.5 μl of binding buffer (50 mM sodium phosphate buffer, 250 mM NaCl, pH 6.0) were added to each well (=1:50 dilution) and mixed well. 50 µl of diluted serum was added to another 96-well v-plate and 150 µl of binding buffer was added (=1:200 dilution). IMAC arrays were pre-activated by adding 50 |||l of 50 mM $CuSO_4$ per well and incubated at RmT for 10 minutes without shaking. The arrays were washed with 150 µl/spot of water by mixing up and down once, then washed with 50 µl of 50 mM NaAc pH 4 per spot, and incubated at RmT for 5 minutes without shaking. They were then washed with 150 µl water/spot twice, by mixing up and down once each time.

IMAC30 chips were equilibrated twice with binding buffer. The chips were incubated for 5 minutes each without shaking. 50 µl of 1:200 diluted serum sample was added to each well and incubate dat RmT for 120 minutes without shaking. The chips were washed three times with 150 µl of binding buffer per well and then "sip and spit" mixed three times, without shaking. The chips were washed with 150 µl of water twice with three mixing cycles, and the bioprocessor reservoir was then removed. The water was aspirated off, and the chips were air dried for ten minutes. One µl of SPA matrix (12.5 mg/ml) in 50% acetonitrile/0.5% TFA water was added per spot, and the chips were air dried for 10 minutes. The application was repeated, and the chips were air dried overnight.

Q-10 Serum profiling Protocol: The samples were diluted into binding buffer. Sample dilution: 1:250 patient serum sample dilution in 100 mM Phosphate buffer (PB), pH 7.0. The Q10 chips were pretreated twice with 150 µl of 100 mM PB, pH 7.0, and incubated five minutes without shaking. 50 µl of 1:250 diluted patient sample was added in each well. The chips were spun at 900 rpm for 45 seconds in a centrifuge and incubated 120 minutes at RmT without shaking. The chips were washed four times with 150 µl of 100 mM PB, pH 7 per well, and three "sip and spit" mixes, without shaking for each wash. The chips were washed with 150 µl of water one time with three mixing cycles. The bioprocessor reservoir was removed, the water was removed, and the chips were air dried for ten minutes. One µl of SPA matrix (12.5 mg/ml) in 50% acetonitrile/0.5% TFA water was added per spot, and the chips were air dried for 10 minutes. The application was repeated, and the chips were air dried overnight.

Urine Profiling: Urine profiling was performed on both the initial set (200 ovarian cancer samples and 50 benign samples) as well as the second set (50 each ovarian cancer, benign, endometrial cancer, and cervical cancer). Samples from the tumor bank were thawed on ice, added to a 96 well plate (following the above mentioned template for arrangement), and centrifuged for 20 minutes at 4000 rpm (urine had not been centrifuged prior to initial freezing and storage in the sample bank). Aliquots of the urine were then put into fresh 96 well plates and stored at −80° C. until use. Two runs of urine profiling were conducted. In the first run, only OvCa and benign samples were used. Samples were profiled on CM 10 and on IMAC-Cu++. The same randomized template that was generated for serum profiling was used; however, there were some samples for which there was not a matching patient urine sample and in these cases, a different patient sample was substituted. Urine samples were profiled (see protocol below) on duplicate ProteinChip Arrays. All replicates were prepared on the same day and were read on a PBSIIc (beginning the morning following preparation) and/or a PCS4000 (beginning a few days after preparation). Arrays were processed with sample using a Biomek 2000 robot. In the second run, endometrial, cervical, benign, and a subgroup of the original OvCa samples (from the first run) were profiled. Samples were profiled on CM10 and on IMAC-$Cu^{++}$. The original randomized template was again used, but 100 of the OvCa samples were substituted with endometrial or cervical urine samples and only 50 of the original set of OvCa samples were included.

CM10 Urine profiling Protocol: 15 µL of urine sample were added to 23 µL of denaturing buffer (9 M urea/2% CHAPS) and incubated for 30 min at 4° C. 263 µl of binding buffer (BB), 100 mM Sodium Acetate pH 4, was added to each denatured sample and mixed well. The chip surface was prepared with two five-minute BB washes. The buffer was removed, and 150 µl of the diluted urine sample was added to each well and incubated at RT with shaking for 30 minutes. The sample was removed and replaced with a fresh 125 µl of the same diluted sample on the appropriate spot, and then incubated at RT with shaking for 30 minutes. The sample was removed, and the chip was washed with thee five-minute BB washes. The buffer was removed, and the chip was washed with water quickly (no incubation) two times. The bioprocessor reservoir was removed, and the chip was air dried. One µl of SPA matrix (12.5 mg/ml) in 50% acetonitrile/0.5% TFA water was added per spot, and the chip was air day for 10 minutes. The application was repeated, and the chips were air dried overnight.

IMAC_$Cu^{++}$ Urine profiling Protocol: 15 µL of urine sample were added to 23 µL of denaturing buffer (9M urea/2% CHAPS). The samples were incubated for 30 minutes at 4° C. 263 ul of binding buffer (BB), 100 mM Sodium Phosphate +0.5 M NaCl pH 7, were added to each denatured sample and mixed well. The IMAC chips were prepared with copper by adding 50 ul of 50 mM $CuSO_4$ per well and incubated at RmT for 10 minutes. The chips were washed with 150 ul/spot of water once for two minutes and incubated with 50 ul of 50 mM NaAc pH4 per spot for five minutes, then washed with water using 150 ul/spot water once for two minutes. The water was removed, and the IMAC30 chips were equilibrated twice for five minutes with binding buffer BB. The buffer was removed, and 150 ul diluted urine sample was added. The chips were incubated at RT with shaking for 30 minutes. The sample was removed and replaced with a fresh 125 ul of the same diluted sample on the appropriate spot, and the chips were incubated at RT with shaking for 30 minutes. The sample was removed, and the chips were washed with BB three times for five minutes. The buffer was removed, and the chips were washed quickly with water twice (no incubation). The bioprocessor reservoir was removed, and the chips were air dried. One ul of SPA matrix (12.5 mg/ml) in 50% acetonitrile/0.5% TFA water was added per spot, and the chips were air dried for 10 minutes. The application was repeated, and the chips were air dried overnight.

Data analysis: Data were acquired using CiphergenExpress software. Mass calibration was performed using external calibrants, intensity normalization was based on total ion current using an external normalization factor, and baseline subtraction was performed. Peak detection was performed in CiphergenExpress software using the criteria that a peak must have a signal/noise ratio of 3:1 and be present in 20% of the spectra. Statistical analysis was performed in CiphergenExpress software using the Mann-Whitney test (for two groups, e.g. benign versus ovarian cancer) or Kruskal-Wallis test (for multiple group comparison, e.g. benign versus ovarian cancer vs endometrial cancer).

Results: The data from the analysis of urine samples (200 ovarian cancer and 50 benign disease) were analyzed first.

TABLE 2

Peaks from with p < .05 using the Mann-Whitney test, when comparing benign versus ovarian cancer.

| Array | p value | AUC | m/z |
|---|---|---|---|
| IMAC30 | 2.52E−04 | 0.664118 | 2785.654 |
| IMAC30 | 8.01E−04 | 0.642618 | 2187.061 |
| IMAC30 | 0.002658 | 0.642618 | 2431.063 |

An AUC>0.5 indicates that the peak is greater in the ovarian cancer group than in the benign group, while an AUC<0.5 indicates that the peak is lower in the ovarian cancer group than in the benign group.

TABLE 3

Peaks with p < .05 for the respective comparisons. Ovarian and endometrial cancer specific markers are defined as peaks with p values < .05 for the comparisons versus benign disease and cervical cancer.

| Condition | Baseline | mass | p values: ovarian vs | | | Median intensity | | | |
|---|---|---|---|---|---|---|---|---|---|
| | | | benign | cervical | endometrial | benign | cervical | endometrial | ovarian |
| | | | Ovarian and endometrial markers | | | | | | |
| IMAC low | 5 | 2193.623 | 0.0023 | 0.0211 | 0.5997 | 10.83 | 15.54 | 23.58 | 28.63 |
| CM10 low | 5 | 2194.852 | 0.0061 | 0.0012 | 0.0855 | 21.61 | 20.34 | 29.83 | 47.21 |
| CM10 low | 5 | 2434.871 | 0.002 | 0.0936 | 0.5628 | 5.459 | 13.16 | 16.13 | 22.21 |
| IMAC low | 5 | 2437.971 | 0.0619 | | | | | | |
| IMAC low | 5 | 2664.621 | 0.01 | 0.0045 | 0.1311 | 1.468 | 1.437 | 1.755 | 2.076 |
| CM10 low | 5 | 2664.983 | 0.0001 | 0.0001 | 0.0132 | 4.211 | 3.612 | 7.373 | 10.96 |
| IMAC low | 5 | 2792.399 | 0.0011 | 0.0311 | 0.9721 | 2.37 | 5.568 | 10.73 | 13.55 |
| CM10 low | 5 | 2793.231 | 0.002 | 0.0004 | 0.0578 | 7.158 | 5.549 | 14.51 | 40.42 |

To determine the specificity of these peaks for ovarian cancer, urine samples from a variety of gynecological cancers (50 ovarian cancer, 50 endometrial cancer, and 50 cervical cancer) and benign pelvic disease (n=50) were profiled. Profiling and data analysis were performed as for the first set, except that the Kruskal-Wallis test was used to test for significance among multiple groups.

Analysis of data obtained from serum samples was performed as for the urine samples. Table 3 shows significant peaks (p<0.05, using the Mann-Whitney test to compare benign versus ovarian cancer) obtained from serum analysis using the IMAC ProteinChip array. As above, an AUC<0.5 indicates that the peak is down-regulated in ovarian cancer while an AUC>0.5 indicates that the peak is up-regulated in ovarian cancer. These peaks were confirmed to represent forms of hepcidin disclosed above. The peak at 2789.4 is hepcidin-25.

TABLE 4

| Mass | P value | AUC | ID comments |
|---|---|---|---|
| 2789.4 | 0.0000069 | 0.70 | hepcidin |

11.2. Purification and Identification of 2789 from MD Anderson Urine Sample:

Urine samples were acquired from the MDACC Ovarian cancer sample bank. The samples had been collected from cancer patients pre-operatively from years 2000 to 2004 and stored at −80° C. Sample distribution was as follows: ovarian cancer (OvCa), 200; endometrial cancer, 50; cervical cancer, 50 and benign, 50. The samples were run in two sets. Experiment #1: The first set comprised the 200 ovarian cancer samples and 50 benign samples. This provided an initial list of candidate biomarkers. Samples profiled on both CM10 and IMAC-Cu. Experiment #2: To test the tumor-type specificity of these candidate biomarkers, a subset (50) of ovarian cancer samples, along with the 50 benign samples, and the 50 endometrial and 50 cervical cancer samples were analyzed. Samples profiled on both CM10 and IMAC-Cu.

1.0 ml of urine was added to 375 ul of IMAC HyperCel (Biosepra) beads which were pre-loaded with copper and incubated at 4.degree. C. for 1 hour. The beads were washed with 350 ul of 100 mM $NaPO_4$, pH7 once, 100 mM NaAc, pH5 twice and organic solvent (33.3% acetonitrile, 16.7% isopropanol and 0.1% TFA) twice. The majority of the 2789 Da marker was present in the organic wash. 5 ul was applied onto NP20 chip (Ciphergen C553-0043). The NP20 chip with 2789 Da on it were treated with SPA (Ciphergen C300-0002) and loaded onto a MicroMass Q-TOF which was equipped with a ProteinChip Interface (Ciphergen Z200-0003). Ions were created using a pulsed nitrogen laser (Laser Science Inc. VSL 337 NDS, Franklin, Mass.) operated at 30 pulses per second delivering an average pulse fluence of 130 mJ/mm.sup.2. Nitrogen gas, at 10 millitorr of pressure, was used for collisional cooling of formed ions and argon was used as collision gas for all low energy collision-induced dissociation experiments. The previously described CHCA matrix system was used for tandem analysis of the acid hydrolysis products. Applied collision energy general followed the rule of 50 eV/kD, and each acquisition was typically the sum of five-minute of spectra. For MS and MS/MS modes, the system was externally calibrated using a mixture of known peptides. The CID spectrum was smoothed and centroided and exported as a sequest file. Protein identification was carried out using Matrix Science Mascot Program (available on the worldwide web at matrixscience.com).

11.3. Purification and Identification of 2789 from JHU Serum Sample:

A total of 178 archived serum specimens were collected at the Johns Hopkins Medical Institutions with institutional approval. The sample set included specimens from 40 healthy women (age, mean±SD, 42±7 years), 40 patients with stage III/IV (23/17 cases) ovarian cancer (age, mean±SD, 56±14 years), groups of 19 patients each with stage 0/I/II/III (3/5/8/3 cases) breast (age, mean±SD, 54±15 years) or stage I/II/III (1/10/8 cases) colon cancers (age, mean±SD, 69±16 years), and groups of 20 patients each with stage I/II/III (1/12/7 cases) prostate (age, mean±SD, 58±8 years), stage II/III (4/16 cases) pancreatic cancers (age, mean±SD, 66±8 years), or diabetes (age, mean±SD, 52±18 years). All patients with breast, colon, pancreatic cancers, and diabetes were female. All above serum samples were processed promptly after collection and stored at −70° C. until use. Additionally, 3 pairs of plasma and serum samples from 3 patients with stage III/IV ovarian cancer (age, mean±SD, 57±13 years) and one serum sample from a healthy control were freshly collected and immediately processed. BD Plus Plastic K2EDTA tubes were used for plasma preparation. All specimens were obtained before treatment and before surgery.

7.5 mg of rabbit anti-ITIH4 antibody (custom made antibody specific against MNFRPGVLSSRQLGLPGPPDVP-DHAAYHPF (SEQ ID NO: 22)) was linked to 12.5 ml of AminoLink® coupling bead (Pierce P/N 20501B). 70 µl serum sample were diluted with 630 µl of PBS pH 7.2 with 0.05% Tween and loaded onto 70 µl of anti-ITIH4 beads. After incubation at 420 C. overnight, the beads were washed with 1 ml of PBS+0.1% Tween buffer three times followed by 1 ml of water wash once. The beads were then eluted with 50 µl of organic elution (33.3% isopropanol/16.7% acetonitrile/0.1% trifluroacetic acid) three times. Flow through the three PBS washes along with organic eluents were profiled onto IMAC30-copper ProteinChip arrays (Ciphergen C553-0078) using a PBS II ProteinChip reader. The 2789 Da protein was present in the flow through as well as all three PBS organic eluents. The flow through fraction form the IP was loaded onto YM10 membrane (Millipore 42407) and 50 µl of flow through fraction from YM10 was profiled on IMAC30 copper (Ciphergen C553-0078) arrays The IMAC30-copper arrays were treated with SPA (Ciphergen C300-0002) and load onto Q-TOF which was equipped with Ciphergen Interface (Ciphergen Z200-0003) for tandem mass spectrometry. In addition, 800 µl eluent from the IP was loaded onto a YM10 membrane (Millipore 42407). the flow through fraction from the YM10 membrane was dried down and rehydrated in 50 µl of 50% acetonitile. 1 µl d of this concentrated eluent was applied onto NP 20 chips with SPA as matrix. This NP20 chips were load onto Q-TOF which was equipped with Ciphergen Interface for tandem mass spectrometry. For MS/MS experiments, spectra were acquired on a Micromass QTOF II tandem mass spectrometer equipped with a Ciphergen (Fremont, Calif.) ProteinChip Array interface (ProteinChip Qq-TOF). Ions were created using a pulsed nitrogen Laser, Laser Science Inc. VSL 337 NDS, (Franklin, Mass.) operated at 30 pulses per second delivering an average pulse fluence of 103 mJ/mm$^2$. Nitrogen gas, at 10 millitorr of pressure, was used for collisional cooling of formed ions and argon was used as collision gas for all low energy collision-induced dissociation experiments. The previously described CHCA matrix system was used for tandem analysis of the acid hydrolysis products. Applied collision energy general followed the rule of 50 eV/kD, and each acquisition was typically the sum of five-minute of spectra. For MS and MS/MS modes, the system was externally calibrated using a mixture of known peptides. The CID spectrum was smoothed and centroided and exported as a sequest file. Protein identification was carried out using Matrix Science Mascot Program (available on line at http://www.matrixscience.com).

11.4. Purification and Identification of 2789 from MD Anderson Serum Sample:

160 ul serum samples were denatured with 240 ul of 9M Urea, 50 mM Tris, pH9, 2% CHAPS at 4.degree. C. for 20 minutes. The denatured serum was loaded onto 720 ul of Q-hyper-DF beads (Biosepra 20078) and incubated at 4.degree. C. for 40 minutes. Twelve fractions were collected in a decreasing stepwise pH gradient. The fractions were profiled on CM10 ProteinChip arrays (Ciphergen C553-007) using a PBS II ProteinChip reader and 2789 Da protein was presented in the flow through. The pH of floe through was then adjusted to pH4 by 1M HOAc and 50 ul was loaded onto CM10 chip. This CM10 chips were treated with SPA (Ciphergen C300-0002) and load onto Q-TOF which was equipped with Ciphergen Interface (Ciphergen Z200-0003) for tandem mass spectrometry. For MS/MS experiments, spectra were acquired on a Micromass QTOF II tandem mass spectrometer equipped with a Ciphergen (Fremont, Calif.) ProteinChip Array interface (ProteinChip Qq-TOF). Ions were created using a pulsed nitrogen Laser, Laser Science Inc. VSL 337 NDS (Franklin, Mass.) operated at 30 pulses per second delivering an average pulse fluence of 130 mJ/mm.sup.2. Nitrogen gas, at 10 millitorr of pressure, was used for collisional cooling of formed ions and argon was used as collision gas for all low energy collision-induced dissociation experiments. The previously described CHCA matrix system was used for tandem analysis of the acid hydrolysis products. Applied collision energy general followed the rule of 50 eV/kD, and each acquisition was typically the sum of five-minute of spectra. For MS and MS/MS modes, the system was externally calibrated using a mixture of known peptides. The CID spectrum was smoothed and centroided and exported as a sequest file. Protein identification was carried out using Matrix Science Mascot Program (available on the worldwide web at matrixscience.com).

11.5. Example 2

Discovery of Biomarkers for Ovarian Cancer

Previous work identified a fragment of inter-alpha trypsin inhibitor heavy chain 4 (ITIH4, also sometimes referred to as ITIH4) as a biomarker with discriminatory power in detecting ovarian cancer. In this example, the correlation networks constructed using expression data of proteins in clinical serum samples that co-precipitate with ITIH4 fragment were analyzed.

The first analysis was done using a panel of 142 serum samples (41 with ovarian cancer, 41 healthy controls, and 20 each with breast, colorectal, and prostate cancers). Expression data were generated in triplicate through immunoprecipitation/pull-down using a polyclonal antibody generated against the ITIH4 3272 m/z fragment, followed by surface-enhanced laser desorption/ionization mass spectrometry. For validation, samples from two additional sites were similarly processed. The first set consisted of 114 ovarian cancer samples (16 pretreatment, 17 post-treatment, 37 cancer-free monitoring cases, and 30 recurrent cases). The second set had 11 ovarian cancer cases, 16 benign cases, and 30 healthy controls.

Using correlation network analysis, in addition to the ITIH4 fragments, a group of four peaks was discovered that were upregulated and highly correlated among 41 ovarian cancer cases, yet under-expressed and minimally correlated among the healthy controls and the other cancer samples. These peaks were further identified as variants of hepcidin. FIG. 2 shows the sequences of various hepcidin fragments, including the four correlated fragments, hepcidin-25, hepcidin-24, hepcidin-22, and hepcidin-20.

Figure 4:
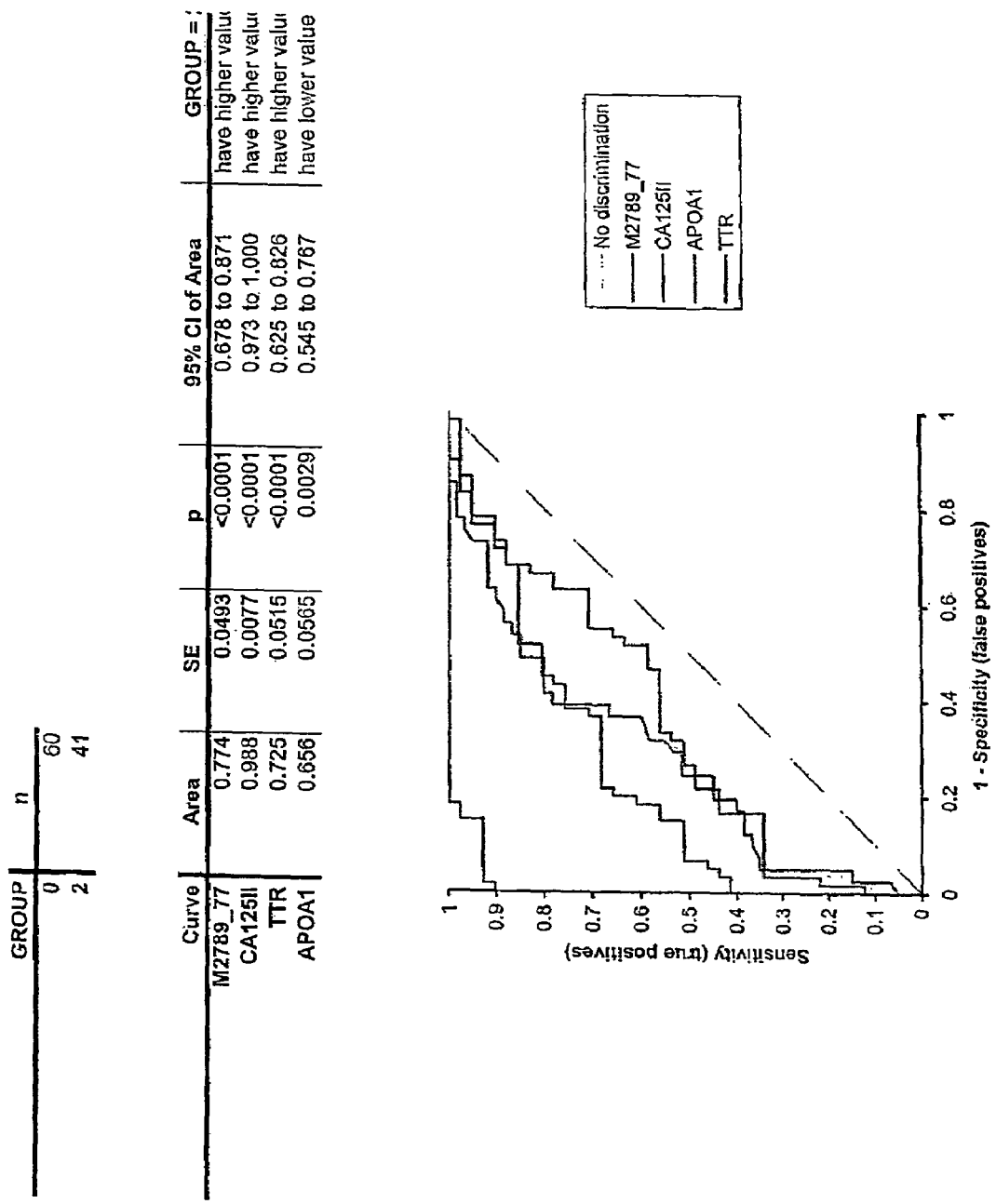
FIG. 4 shows ROC curve analysis showing the power of the hepcidin peak at m/z 2789 has in differentiating ovarian cancer from other cancers. The AUC is 0.774 and is significantly greater than 0.5 with p-value <0.0001.
Figure 5:
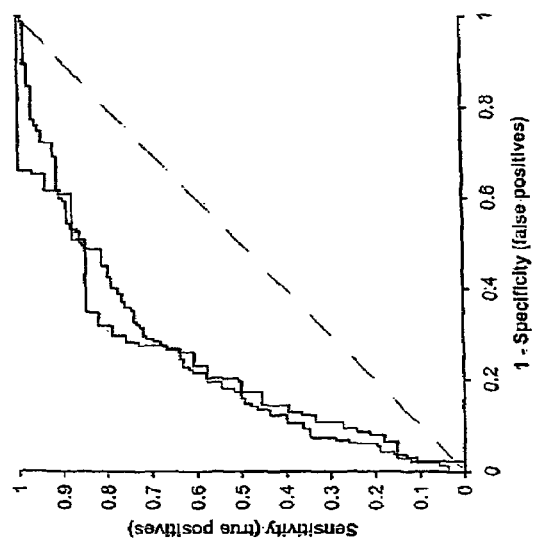
FIG. 5 shows ROC curve analysis showing the power of the hepcidin peak for the two independent validation sets. The AUCs are 0.756 and 0.772, both greater than 0.5 with p-value <0.0001.

Among the 142 samples, receiver-operating-characteristic (ROC) curve analysis showed that the peak corresponding to the full-length hepcidin had an area-under-curve (AUC) of 0.876 (95% CI: 0.795-0.957) in separating ovarian cancer from healthy controls (see FIG. 1) and 0.774 (0.678-0.871) in separating ovarian cancer from the other three types of cancers (see FIG. 4). In the first validation set, hepcidin was higher in the pretreatment and recurrent groups than in the post-treatment and cancer-free monitoring groups (AUC=0.756 (0.702-0.811)), with the recurrent cases having the highest hepcidin levels (see FIG. 5). In the second validation set, the AUC was 0.722 (0.693-0.851) in separating ovarian cancer from benign and healthy controls (for both validation sets, all triplicates were included in the analysis; see FIG. 5). Preliminary results indicated that hepcidin and ITIH4 fragment are binding partners.

In the first approach, 10 ul of serum was added to 10 ul of ITIH4 beads in 90 ul PBS with 0.05% Triton. The beads were incubated overnight at 4° C. At this stage, the flow-through (100 ul) was removed, and 5 ul was analyzed on IMAC and CM10 chips. The beads were washed three times with 150 ul PBS with 0.1% Triton. After each wash, 20 ul wash buffer was removed and analyzed on IMAc and CM10 chips. The beads were eluted after each wash with 50 ul organic elution buffer. 50 ul of the total eluent was then analyzed on IMAc and CM10 chips. In a second approach, samples from the ITIH4 IP flow through fraction A13 were concentrated and analyzed on IMAC chips.

Figure 3:
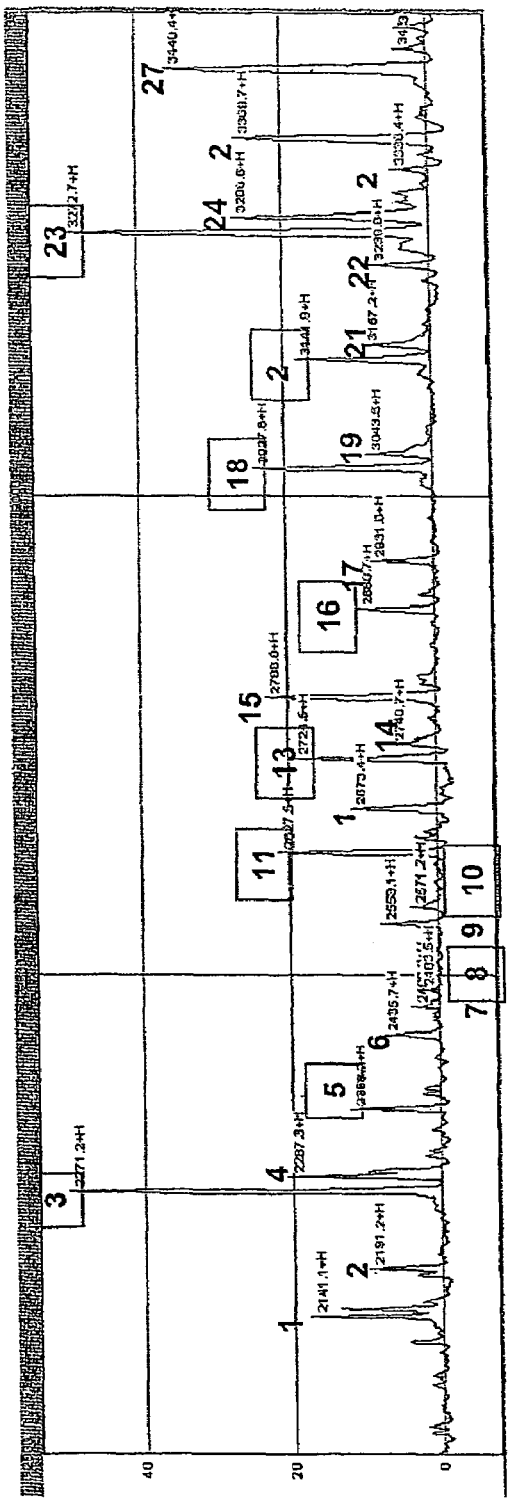
FIG. 3 shows the SELDI spectrum of the serum sample after immunoprecipitation/pull-down using an antibody against ITIH4 fragment (m/z 3272). Peaks with rectangle labels are known fragments of ITIH4. The four discovered hepcidin variants are in this spectrum at approximate m/z locations 2191, 2436, 2673, and 2788 (indicated by arrows).
Figure 6:
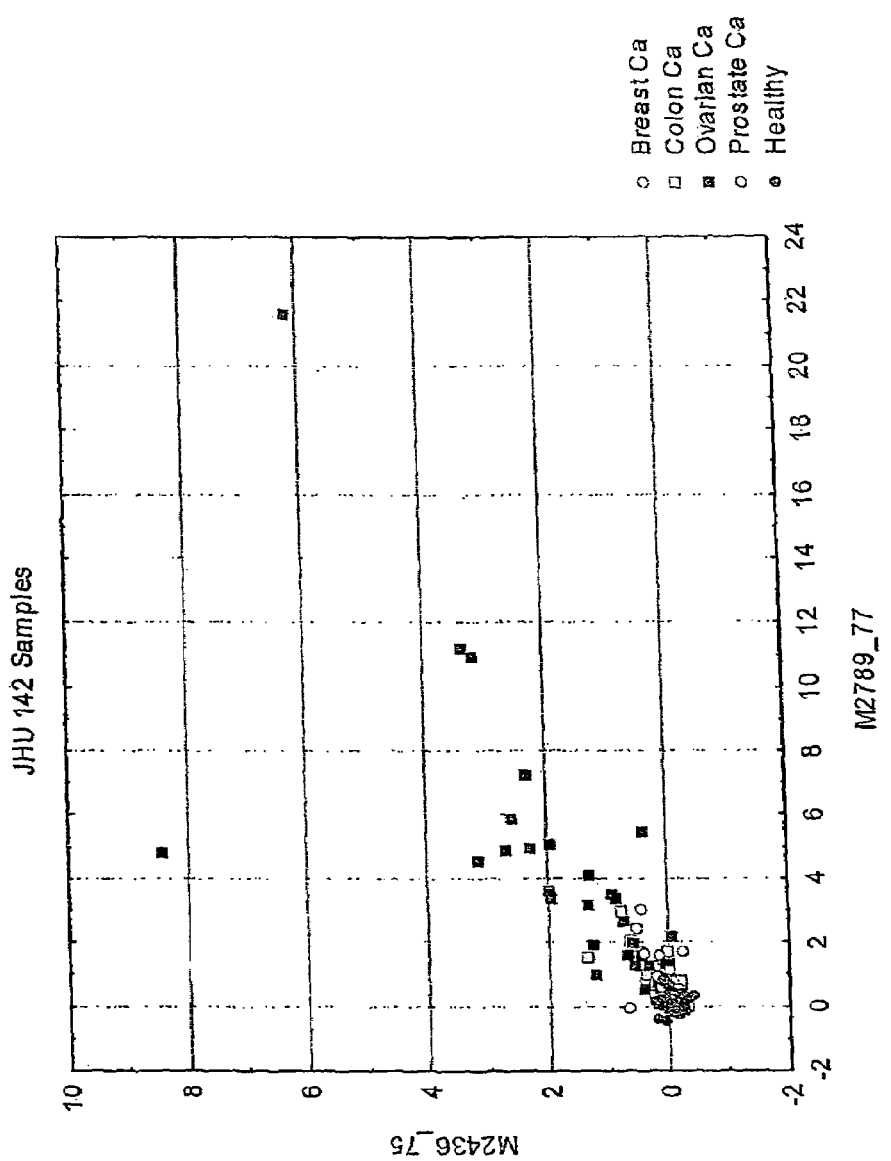
FIG. 6 shows a scatterplot of the five groups of samples in two of the four peaks representing hepcidin variants.
Figure 8:
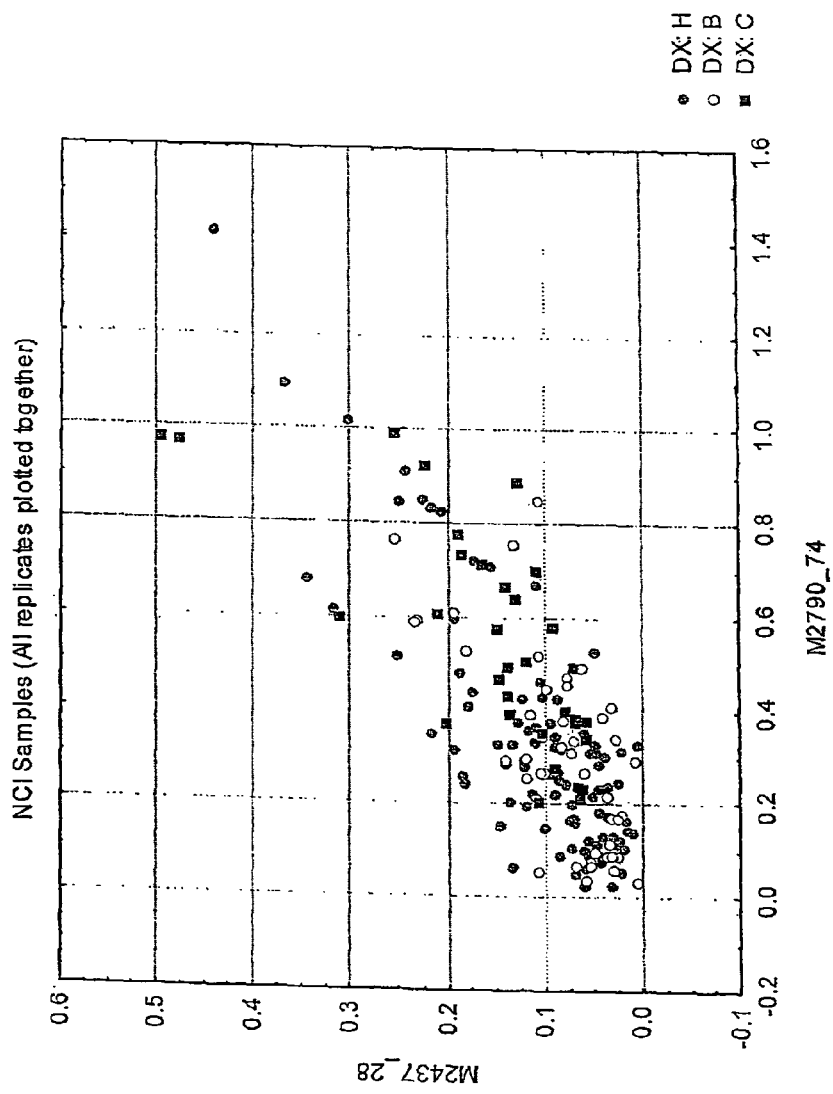
FIG. 8 shows a scatterplot of five groups of patients from a second independent validation set using two of the hepcidin peaks. It shows that these peaks are lower in healthy controls and patients with benign diseases, and are higher in patients with ovarian cancer.
Figure 9E:
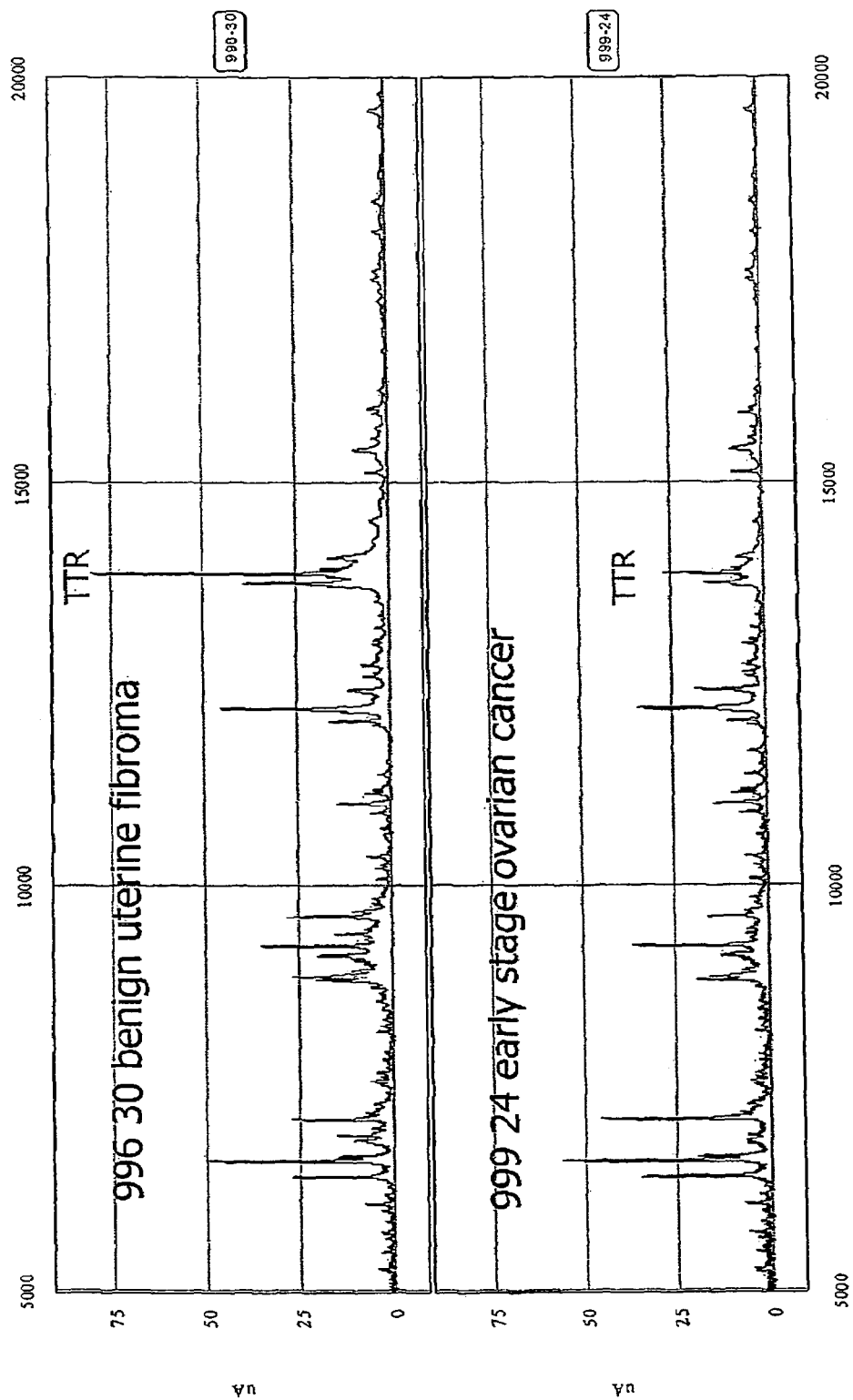
Figure 11:
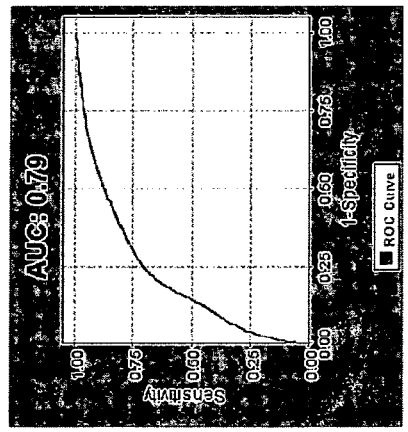
FIG. 11 shows ROC curve analysis showing the mini-assay of Example 4, which follows.

FIG. 3 shows the SELDI spectrum of the serum sample after immunoprecipitation/pull-down using the antibody against ITIH4 fragment. Correlation network analysis showed that the four peaks (m/z 2191, 2436, and 2788) are highly correlated among themselves and inversely correlated with the group of ITIH4 fragments in serum samples from ovarian cancer patients. The correlation is not as strong among healthy controls. Similar correlation network analysis was performed between ovarian cancer, prostate cancer, breast cancer, and healthy controls. The strongest correlation among the four peaks was the one with ovarian cancer. FIG. 6 shows a scatterplot of the five groups of samples in two of the four peaks representing hepcidin variants. FIG. 7 shows a scatterplot of five groups of patients from an independent validation set using two of the hepcidin peaks. It shows that these peaks are lower in patients free of cancer and patients after treatment, and are higher in patients with ovarian cancer pretreatment, as well as in those with recurrent ovarian cancer. The hepcidin level correlates with the tumor load. FIG. 8 shows a scatterplot of five groups of patients from a second independent validation set using two of the hepcidin peaks. It shows that these peaks are lower in healthy controls and patients with benign diseases, and are higher in patients with ovarian cancer.

11.6. Example 3

Biomarker Assay Using Large Sample Set

To further evaluate the quality of hepcidin as an ovarian cancer marker, a large multi-institutional study was performed. A total of 607 serum samples from five sites were analyzed using SELDI TOF-MS protocols optimized for the seven biomarkers. They included 234 women with benign gynecologic diseases, and 373 patients with invasive epithelial ovarian cancer (101 early stage, 231 late stage, and 40 stage unknown). Among them, 165 benigns and 228 cancers had a CA125 available at time of analysis. The median and quartiles of CA125 for benign, early stage, and late or unknown stage were 26/11/57 IU, 80/22/434 IU, and 234/40/1114 IU, respectively. The biomarkers were assessed individually using the Mann-Whitney U Test. A linear composite index was derived in an unsupervised fashion using data from one site and then calculated for the remaining data using the fixed formula. ROC curve analyses were performed on data from individual sites and all sites combined.

A total of 607 serum samples from five sites were analyzed using SELDI TOF-MS protocols optimized for seven biomarkers: hepcidin-25 (M2789), cysteinylated transthyretin, Apo A1 (M28043), transferrin (M79K), CTAP-III (M9313.9), ITIH4 fragment 1 (M3272) and β2-microglobulin (M11.7K) ("the seven marker panel"). They included 234 women with benign gynecologic diseases, and 373 patients with invasive epithelial ovarian cancer (101 early stage, 231 late stage, and 40 stage unknown). Among them, 165 benigns and 228 cancers had a CA125 available at time of analysis. The median and quartiles of CA125 for benign, early stage, and late or unknown stage were 26/11/57 IU, 80/22/434 IU, and 34/40/1114 IU, respectively. The biomarkers were assessed individually using the Mann-Whitney U Test. A linear composite index was derived in an unsupervised fashion using data from one site and then calculated for the remaining data using the fixed formula. ROC curve analyses were performed on data from individual sites and all sites combined. All seven biomarkers individually demonstrated statistically significant differentiating power, and the majority had p-value<0.00001. AUCs of the composite index in ROC analyses for the six sites were 0.602, 0.566, 0.821, 0.813, and 0.592 in detecting cancer at all stages from benign. On the combined data, the differences in AUC between the index and CA125 were not statistically significant for the detection of cancer at all stages (AUC=0.706 vs. 0.725) or early stages only (AUC=0.534 vs. 0.653). However, the index did better at the high-sensitivity range. At a fixed sensitivity of 86%, the specificity of the index was 34% (77/226) compared to CA125 at 26% (42/163). For early stage cases, at a fixed sensitivity of 84%, the specificity of the index was 24% (55/226) compared to CA125 at 14%% (22/163).

11.7. Example 4

Biomarker Assay Using Smaller Sample Set

Pre-operative serum samples from 202 consecutive patients being evaluated for ovarian pathology were aliquotted, and frozen within six hours of collection. The serum samples were evaluated using a SELDI-TOF-MS proteomics assay for the seven marker panel. 126 samples were used to train a model and the remaining samples were used for blinded testing. Of the 202 patients, 132 had benign disease (including endometriosis, benign pelvic cyst, uterine fibromas), 11 had borderline tumors, 50 had invasive epithelial ovarian cancer, 3 had germ cell tumors, and the remaining had metastatic non-gynecologic cancers. The median age in the benign disease group was 48.3 years (range 20-84), and 65.1 years (range 40-89) in the invasive ovarian cancer group.

Pre-operative serum samples from 202 consecutive patients being evaluated for ovarian pathology were aliquotted, and frozen within six hours of collection. The serum samples were evaluated using a SELDI-TOF-MS proteomics assay for the seven marker panel. 126 samples were used to train a model and the remaining samples were used for blinded testing. Of the 202 patients, 132 had benign disease (including endometriosis, benign pelvic cyst, uterine fibromas), 11 had borderline tumors, 50 had invasive epithelial ovarian cancer, 3 had germ cell tumors, and the remaining had metastatic non-gynecologic cancers. The median age in the benign disease group was 48.3 years (range 20-84), and 65.1 years (range 40-89) in the invasive ovarian cancer group. In the training set, CA125 had a sensitivity of 100% (95% CI: 88.1-100.0%) and specificity of 63.3% (95% CI: 52.2-73.3%), while in the test set, CA125 had a sensitivity of 95.0% (95% CI: 75.1-99.9%) and specificity of 67.5% (95% CI: 50.9-81.4%). A multivariable algorithm incorporating the seven markers and CA125 had a sensitivity of 86.2% (95% CI: 68.3-96.1%) and specificity of 94.4% (95% CI: 87.5-98.2%) in the training set and a sensitivity of 80.0% (95% CI: 68.3-96.1%) and specificity of 90.0% (95% CI: 76.4-97.2%) in the test set. The seven marker panel may be useful in helping triage patients being evaluated for a persistent pelvic mass. This marker panel improves specificity of CA125, although diminishes its sensitivity.

For the following panels, the sensitivity is 85.2% with 95% CI 65.4%~95.1%; the specificity is 96.7% with 95% CI 89.9%~99.1%.

3 markers:
Apo, transthyretin, ITIH4
Apo, transthyretin, transferrin
4 markers:
Apo, transthyretin, ITIH4, transferrin
Apo, transthyretin, ITIH4, CTAP-III
5 markers:
Apo, transthyretin, ITIH4, transferrin, CTAP-III
Apo, transthyretin, ITIH4, transferrin, β2 microglobulin
6 markers:
Apo, transthyretin, ITIH4, transferrin, CTAP-III, β2 microglobulin For the following panels, the sensitivity is 81.5% with 95% CI 61.3%~93.0%; the specificity is 97.8% with 95% CI 91.4%~99.6%.

3 markers:
Apo, transthyretin, hepcidin
4 markers:
Apo, transthyretin, hepcidin, transferrin
Apo, transthyretin, hepcidin, CTAP-III
5 markers:
Apo, transthyretin, hepcidin, transferrin, CTAP-III
Apo, transthyretin, hepcidin, transferrin, β2 microglobulin
6 markers:
Apo, transthyretin, hepcidin, transferrin, CTAP-III, β2 microglobulin It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

What is claimed is:

1. A method for qualifying ovarian cancer status in a subject comprising: (a) measuring the level of hepcidin in a biological sample from the subject being screened for ovarian cancer; and (b) correlating the measurement of an increased level of hepcidin in the biological sample from the subject as compared to the level of hepcidin in a biological sample from a healthy subject with the diagnosis of ovarian cancer.

2. The method of claim 1, wherein the level of hepcidin is measured by mass spectrometry.

3. The method of claim 2, wherein mass spectrometry is SELDI-MS.

4. The method of claim 1, wherein the level of hepcidin is measured by immunoassay.

5. The method of claim 1, wherein the sample is blood or a blood derivative.

6. The method of claim 1, wherein the sample is ovarian cyst fluid, ascites, or urine.

7. The method of claim 1, wherein the correlating is performed by executing a software classification algorithm.

8. The method of claim 1, wherein ovarian cancer is stage I or II ovarian cancer.

9. The method of claim 1, wherein the subject has been treated for ovarian cancer and the ovarian cancer is recurrence of cancer.

10. The method of claim 1, wherein non-ovarian cancer is a gynecological condition selected from benign ovarian cyst, endometriosis, uterine fibroma, breast cancer and cervical cancer.

11. The method of claim 1, further comprising: (c) reporting the status to the subject.

12. The method of claim 1, further comprising: recording the status on a tangible medium.

13. The method of claim 1, further comprising: (c) managing subject treatment based on the status.

14. The method of claim 13, further comprising: (d) measuring the level of hepcidin after subject management and correlating the measurement with disease progression.

* * * * *

SEQUENCE LISTING

```
<160> NUMBER OF SEQ ID NOS: 25

<210> SEQ ID NO 1
<211> LENGTH: 37
<212> TYPE: PRT
<213> ORGANISM: Homo sapiens

<400> SEQUENCE: 1

Ser Trp Met Pro Met Phe Gln Arg Arg Arg Arg Asp Thr His Phe
 1               5                  10                  15

Pro Ile Cys Ile Phe Cys Cys Gly Cys Cys His Arg Ser Lys Cys Gly
                20                  25                  30

Met Cys Cys Lys Thr
         35

<210> SEQ ID NO 2
<211> LENGTH: 36
<212> TYPE: PRT
<213> ORGANISM: Homo sapiens

<400> SEQUENCE: 2

Trp Met Pro Met Phe Gln Arg Arg Arg Arg Asp Thr His Phe Pro
 1               5                  10                  15

Ile Cys Ile Phe Cys Cys Gly Cys Cys His Arg Ser Lys Cys Gly Met
                20                  25                  30

Cys Cys Lys Thr
         35

<210> SEQ ID NO 3
<211> LENGTH: 35
<212> TYPE: PRT
<213> ORGANISM: Homo sapiens
```

```
<400> SEQUENCE: 3

Met Pro Met Phe Gln Arg Arg Arg Arg Asp Thr His Phe Pro Ile
 1               5                  10                  15

Cys Ile Phe Cys Cys Gly Cys Cys His Arg Ser Lys Cys Gly Met Cys
                20                  25                  30

Cys Lys Thr
         35

<210> SEQ ID NO 4
<211> LENGTH: 34
<212> TYPE: PRT
<213> ORGANISM: Homo sapiens

<400> SEQUENCE: 4

Pro Met Phe Gln Arg Arg Arg Arg Asp Thr His Phe Pro Ile Cys
 1               5                  10                  15

Ile Phe Cys Cys Gly Cys Cys His Arg Ser Lys Cys Gly Met Cys Cys
                20                  25                  30

Lys Thr

<210> SEQ ID NO 5
<211> LENGTH: 33
<212> TYPE: PRT
<213> ORGANISM: Homo sapiens

<400> SEQUENCE: 5

Met Phe Gln Arg Arg Arg Arg Asp Thr His Phe Pro Ile Cys Ile
 1               5                  10                  15

Phe Cys Cys Gly Cys Cys His Arg Ser Lys Cys Gly Met Cys Cys Lys
                20                  25                  30

Thr

<210> SEQ ID NO 6
<211> LENGTH: 32
<212> TYPE: PRT
<213> ORGANISM: Homo sapiens

<400> SEQUENCE: 6

Phe Gln Arg Arg Arg Arg Asp Thr His Phe Pro Ile Cys Ile Phe
 1               5                  10                  15

Cys Cys Gly Cys Cys His Arg Ser Lys Cys Gly Met Cys Cys Lys Thr
                20                  25                  30

<210> SEQ ID NO 7
<211> LENGTH: 31
<212> TYPE: PRT
<213> ORGANISM: Homo sapiens

<400> SEQUENCE: 7

Gln Arg Arg Arg Arg Asp Thr His Phe Pro Ile Cys Ile Phe Cys
 1               5                  10                  15

Cys Gly Cys Cys His Arg Ser Lys Cys Gly Met Cys Cys Lys Thr
                20                  25                  30

<210> SEQ ID NO 8
<211> LENGTH: 30
<212> TYPE: PRT
<213> ORGANISM: Homo sapiens

<400> SEQUENCE: 8
```

-continued

Arg Arg Arg Arg Arg Asp Thr His Phe Pro Ile Cys Ile Phe Cys Cys
1               5                   10                  15

Gly Cys Cys His Arg Ser Lys Cys Gly Met Cys Cys Lys Thr
            20                  25                  30

<210> SEQ ID NO 9
<211> LENGTH: 29
<212> TYPE: PRT
<213> ORGANISM: Homo sapiens

<400> SEQUENCE: 9

Arg Arg Arg Arg Asp Thr His Phe Pro Ile Cys Ile Phe Cys Cys Gly
1               5                   10                  15

Cys Cys His Arg Ser Lys Cys Gly Met Cys Cys Lys Thr
            20                  25

<210> SEQ ID NO 10
<211> LENGTH: 28
<212> TYPE: PRT
<213> ORGANISM: Homo sapiens

<400> SEQUENCE: 10

Arg Arg Arg Asp Thr His Phe Pro Ile Cys Ile Phe Cys Cys Gly Cys
1               5                   10                  15

Cys His Arg Ser Lys Cys Gly Met Cys Cys Lys Thr
            20                  25

<210> SEQ ID NO 11
<211> LENGTH: 27
<212> TYPE: PRT
<213> ORGANISM: Homo sapiens

<400> SEQUENCE: 11

Arg Arg Asp Thr His Phe Pro Ile Cys Ile Phe Cys Cys Gly Cys Cys
1               5                   10                  15

His Arg Ser Lys Cys Gly Met Cys Cys Lys Thr
            20                  25

<210> SEQ ID NO 12
<211> LENGTH: 26
<212> TYPE: PRT
<213> ORGANISM: Homo sapiens

<400> SEQUENCE: 12

Arg Asp Thr His Phe Pro Ile Cys Ile Phe Cys Cys Gly Cys Cys His
1               5                   10                  15

Arg Ser Lys Cys Gly Met Cys Cys Lys Thr
            20                  25

<210> SEQ ID NO 13
<211> LENGTH: 25
<212> TYPE: PRT
<213> ORGANISM: Homo sapiens

<400> SEQUENCE: 13

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 14
<211> LENGTH: 24

```
<212> TYPE: PRT
<213> ORGANISM: Homo sapiens

<400> SEQUENCE: 14

Thr His Phe Pro Ile Cys Ile Phe Cys Cys Gly Cys Cys His Arg Ser
 1               5                  10                  15

Lys Cys Gly Met Cys Cys Lys Thr
            20

<210> SEQ ID NO 15
<211> LENGTH: 23
<212> TYPE: PRT
<213> ORGANISM: Homo sapiens

<400> SEQUENCE: 15

His Phe Pro Ile Cys Ile Phe Cys Cys Gly Cys Cys His Arg Ser Lys
 1               5                  10                  15

Cys Gly Met Cys Cys Lys Thr
            20

<210> SEQ ID NO 16
<211> LENGTH: 22
<212> TYPE: PRT
<213> ORGANISM: Homo sapiens

<400> SEQUENCE: 16

Phe Pro Ile Cys Ile Phe Cys Cys Gly Cys Cys His Arg Ser Lys Cys
 1               5                  10                  15

Gly Met Cys Cys Lys Thr
            20

<210> SEQ ID NO 17
<211> LENGTH: 21
<212> TYPE: PRT
<213> ORGANISM: Homo sapiens

<400> SEQUENCE: 17

Pro Ile Cys Ile Phe Cys Cys Gly Cys Cys His Arg Ser Lys Cys Gly
 1               5                  10                  15

Met Cys Cys Lys Thr
            20

<210> SEQ ID NO 18
<211> LENGTH: 20
<212> TYPE: PRT
<213> ORGANISM: Homo sapiens

<400> SEQUENCE: 18

Ile Cys Ile Phe Cys Cys Gly Cys Cys His Arg Ser Lys Cys Gly Met
 1               5                  10                  15

Cys Cys Lys Thr
            20

<210> SEQ ID NO 19
<211> LENGTH: 19
<212> TYPE: PRT
<213> ORGANISM: Homo sapiens

<400> SEQUENCE: 19

Cys Ile Phe Cys Cys Gly Cys Cys His Arg Ser Lys Cys Gly Met Cys
 1               5                  10                  15

Cys Lys Thr
```

<210> SEQ ID NO 20
<211> LENGTH: 18
<212> TYPE: PRT
<213> ORGANISM: Homo sapiens

<400> SEQUENCE: 20

Cys Ile Phe Cys Cys Gly Cys Cys His Arg Ser Lys Cys Gly Met Cys
 1               5                  10                  15

Cys Lys

<210> SEQ ID NO 21
<211> LENGTH: 17
<212> TYPE: PRT
<213> ORGANISM: Homo sapiens

<400> SEQUENCE: 21

Cys Ile Phe Cys Cys Gly Cys Cys His Arg Ser Lys Cys Gly Met Cys
 1               5                  10                  15

Cys

<210> SEQ ID NO 22
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met Asn Phe Arg Pro Gly Val Leu Ser Ser Arg Gln Leu Gly Leu Pro
 1               5                  10                  15

Gly Pro Pro Asp Val Pro Asp His Ala Ala Tyr His Pro Phe
            20                  25                  30

<210> SEQ ID NO 23
<211> LENGTH: 30
<212> TYPE: PRT
<213> ORGANISM: Homo sapiens

<400> SEQUENCE: 23

Met Asn Phe Arg Pro Gly Val Leu Ser Ser Arg Gln Leu Gly Leu Pro
 1               5                  10                  15

Gly Pro Pro Asp Val Pro Asp His Ala Ala Tyr His Pro Phe
            20                  25                  30

<210> SEQ ID NO 24
<211> LENGTH: 26
<212> TYPE: PRT
<213> ORGANISM: Homo sapiens

<400> SEQUENCE: 24

Pro Gly Val Leu Ser Ser Arg Gln Leu Gly Leu Pro Gly Pro Pro Asp
 1               5                  10                  15

Val Pro Asp His Ala Ala Tyr His Pro Phe
            20                  25

<210> SEQ ID NO 25
<211> LENGTH: 25
<212> TYPE: PRT
<213> ORGANISM: Homo sapiens

<400> SEQUENCE: 25

-continued

```
Gly Val Leu Ser Ser Arg Gln Leu Gly Leu Pro Gly Pro Pro Asp Val
 1               5                  10                  15

Pro Asp His Ala Ala Tyr His Pro Phe
            20              25
```